US012605384B2

(12) United States Patent
Kass et al.

(10) Patent No.: US 12,605,384 B2
(45) **Date of Patent: *Apr. 21, 2026**

(54) USES

(71) Applicant: INTRA-CELLULAR THERAPIES, INC., New York, NY (US)

(72) Inventors: David Kass, New York, NY (US); Toru Hashimoto, New York, NY (US); Lawrence P. Wennogle, Hillsborough, NJ (US); Joseph Hendrick, New York, NY (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,406

(22) Filed: Jun. 29, 2023

(65) Prior Publication Data

US 2023/0338385 A1 Oct. 26, 2023

Related U.S. Application Data

(60) Division of application No. 16/892,206, filed on Jun. 3, 2020, now Pat. No. 11,759,465, which is a continuation-in-part of application No. PCT/US2019/016128, filed on Jan. 31, 2019.

(60) Provisional application No. 62/700,126, filed on Jul. 18, 2018, provisional application No. 62/683,431, filed on Jun. 11, 2018, provisional application No. 62/624,705, filed on Jan. 31, 2018.

(51) Int. Cl.

| | |
|---|---|
| ***A61K 31/519*** | (2006.01) |
| ***A61K 9/00*** | (2006.01) |
| ***A61K 31/04*** | (2006.01) |
| ***A61K 31/197*** | (2006.01) |
| ***A61K 31/216*** | (2006.01) |
| ***A61K 31/41*** | (2006.01) |
| ***A61K 31/4178*** | (2006.01) |
| ***A61K 31/7056*** | (2006.01) |
| ***A61K 45/06*** | (2006.01) |
| ***A61P 9/04*** | (2006.01) |

(52) U.S. Cl.

CPC .......... *A61K 31/519* (2013.01); *A61K 9/0053* (2013.01); *A61K 31/04* (2013.01); *A61K 31/197* (2013.01); *A61K 31/216* (2013.01); *A61K 31/41* (2013.01); *A61K 31/4178* (2013.01); *A61K 31/7056* (2013.01); *A61K 45/06* (2013.01); *A61P 9/04* (2018.01)

(58) Field of Classification Search

CPC .... A61K 31/41; A61K 31/216; A61K 31/197; A61K 31/519

See application file for complete search history.

(56) References Cited

U.S. PATENT DOCUMENTS

| | | | |
|---|---|---|---|
| 4,666,908 | A | 5/1987 | Hamilton |
| 4,722,810 | A | 2/1988 | Delaney et al. |
| 4,929,641 | A | 5/1990 | Haslanger et al. |
| 5,202,328 | A | 4/1993 | de Laszlo et al. |
| 5,217,996 | A | 6/1993 | Ksander |
| 5,242,901 | A | 9/1993 | Speyer et al. |
| 5,294,612 | A | 3/1994 | Bacon et al. |
| 5,393,755 | A | 2/1995 | Neustadt et al. |
| 5,824,683 | A | 10/1998 | McKittrick et al. |
| 5,849,770 | A | 12/1998 | Head et al. |
| 5,939,419 | A | 8/1999 | Tulshian et al. |
| 5,962,492 | A | 10/1999 | Warrellow et al. |
| 6,013,621 | A | 1/2000 | Nishi et al. |
| 6,133,273 | A | 10/2000 | Gilbert et al. |
| 6,221,335 | B1 | 4/2001 | Foster |
| 6,235,742 | B1 | 5/2001 | Bell et al. |
| 6,235,746 | B1 | 5/2001 | Davis et al. |
| 6,316,444 | B1 | 11/2001 | Hunt et al. |
| 6,334,997 | B1 | 1/2002 | Foster et al. |
| 6,423,716 | B1 | 7/2002 | Matsuno et al. |
| 6,440,710 | B1 | 8/2002 | Keinan et al. |
| 6,492,371 | B2 | 12/2002 | Roylance |
| 6,498,165 | B1 | 12/2002 | Armstrong et al. |
| 6,552,029 | B1 | 4/2003 | Davis et al. |

(Continued)

FOREIGN PATENT DOCUMENTS

| | | | |
|---|---|---|---|
| DE | 19931206 | A1 | 1/2001 |
| DE | 10 2005 042 877 | A1 | 3/2007 |

(Continued)

OTHER PUBLICATIONS

Adamo et al., “Molecular targets for PDE inhibitor-mediated improvement of cardiac dysfunction in the mdx mouse?”, BMC Pharmacology, 2011, 11(Suppl 1):O20 (Abstract Only).

Ahn, H. et al., “Potent Tetracyclic Guanine Inhibitors of PDE1 and PDE5 Cyclic Guanosine Monophosphate Phosphodiesterases with Oral Antihypertensive Activity,” Journal of Medicinal Chemistry, 1997, 40 (14), 2196-2210.

Al-Afaleq, E. et al., “Heterocyclic o-Aminonitriles: Preparation of Pyrazolo[3,4-d]-pyrimidines with Modification of the Substituents at the 1-Position,” Molecules, 2001, 6, 621-638.

“Anxiety,” [retrieved on May 14, 2008]. Retrieved online via Internet, URL: http://www.nlm.nih.gov/medlineplus/anxiety.html, 5 pages.

(Continued)

*Primary Examiner* — Marcos L Sznaidman

(74) *Attorney, Agent, or Firm* — Hoxie & Associates LLC

(57) ABSTRACT

The disclosure provides methods, treatments and materials for enhancing the effect of an adenosine $A_2$ receptor agonist in the treatment, mitigation or prophylaxis of a disease or condition characterized by inotropic and/or lusitropic dysfunction, and/or enhancing adenosine $A_2$ receptor function in the treatment, mitigation or prophylaxis of a disease or condition characterized by impaired adenosine $A_2$ receptor function, comprising administration of an effective amount of a PDE1 inhibitor to a patient in need thereof, for example a patient suffering from heart failure.

22 Claims, No Drawings

(56) References Cited

U.S. PATENT DOCUMENTS 6,586,423 B2 7/2003 Bilodeau et al.
6,599,908 B1 7/2003 Davis et al.
6,603,008 B1 8/2003 Ando et al.
6,649,608 B2 11/2003 Pease et al.
6,670,368 B1 12/2003 Breault et al.
6,693,099 B2 2/2004 Degenhardt et al.
6,756,373 B1 6/2004 Allerton et al.
6,969,719 B2 11/2005 Asberom et al.
7,153,824 B2 12/2006 Palmer et al.
7,157,451 B2 1/2007 Atwal et al.
7,230,031 B2 6/2007 Siohara et al.
7,517,990 B2 4/2009 Ito et al.
7,964,607 B2 6/2011 Verhoest et al.
8,273,750 B2 9/2012 Li et al.
8,273,751 B2 9/2012 Li et al.
8,513,244 B2 8/2013 Gendron et al.
8,536,159 B2 9/2013 Li et al.
8,633,180 B2 1/2014 Li et al.
8,664,207 B2 3/2014 Li et al.
8,697,710 B2 4/2014 Li et al.
8,703,934 B2 4/2014 Nell et al.
8,829,008 B2 9/2014 Li et al.
8,846,693 B2 9/2014 Li et al.
8,858,911 B2 10/2014 Li et al.
8,859,564 B2 10/2014 Li et al.
8,927,556 B2 1/2015 Li et al.
9,000,001 B2 4/2015 Li et al.
9,006,258 B2 4/2015 Fienberg et al.
9,073,936 B2 7/2015 Li et al.
9,157,906 B2 10/2015 Greengard et al.
9,198,924 B2 12/2015 Mates et al.
9,255,099 B2 2/2016 Li et al.
9,371,327 B2 6/2016 Li et al.
9,403,836 B2 8/2016 Li
9,434,730 B2 9/2016 Li et al.
9,468,637 B2 10/2016 Fienberg et al.
9,469,647 B2 10/2016 Li et al.
9,487,527 B2 11/2016 Li et al.
9,546,175 B2 1/2017 Li et al.
9,624,230 B2 4/2017 Li et al.
9,763,948 B2 9/2017 Li et al.
9,801,882 B2 10/2017 Wennogle et al.
9,884,872 B2 2/2018 Li et al.
2003/0069246 A1 4/2003 Darrow et al.
2003/0092908 A1 5/2003 Pitts et al.
2003/0162782 A1 8/2003 Grossman et al.
2003/0211040 A1 11/2003 Greengard et al.
2004/0087517 A1 5/2004 Burnet et al.
2004/0259792 A1 12/2004 Palmer et al.
2005/0075795 A1 4/2005 Pandit
2005/0113379 A1 5/2005 Ge et al.
2006/0041014 A1 2/2006 Naylor et al.
2006/0252790 A1 11/2006 Allen et al.
2007/0082929 A1 4/2007 Gant et al.
2007/0197695 A1 8/2007 Potyen et al.
2008/0096870 A1 4/2008 Martynyuk et al.
2008/0176961 A1 7/2008 Greengard et al.
2008/0188492 A1 8/2008 Li et al.
2008/0193964 A1 8/2008 Greengard et al.
2008/0194592 A1 8/2008 Mates et al.
2010/0069768 A1* 3/2010 Min ...................... A61N 1/365
600/528
2010/0087450 A1 4/2010 Mates et al.
2010/0173878 A1 7/2010 Li et al.
2010/0273753 A1 10/2010 Li et al.
2010/0273754 A1 10/2010 Li
2010/0323997 A1 12/2010 Fienberg et al.
2011/0190373 A1 8/2011 Yan et al.
2011/0237561 A1 9/2011 Li et al.
2011/0245214 A1 10/2011 Li et al.
2011/0281832 A1 11/2011 Li et al.
2011/0312978 A1 12/2011 Davis et al.
2012/0053190 A1 3/2012 Fienberg et al.
2012/0070443 A1 3/2012 Movesian
2012/0071450 A1 3/2012 Li et al.
2012/0094966 A1 4/2012 Li et al.
2012/0136013 A1 5/2012 Li et al.
2012/0201754 A1 8/2012 Li
2012/0238589 A1 9/2012 Li
2013/0018063 A1 1/2013 Li et al.
2013/0085123 A1 4/2013 Li et al.
2013/0149309 A1 6/2013 Greengard et al.
2013/0239234 A1 9/2013 Greengard et al.
2013/0324565 A1 12/2013 Li et al.
2013/0330365 A1 12/2013 Hughes et al.
2013/0331363 A1 12/2013 Li et al.
2013/0338124 A1 12/2013 Li et al.
2014/0005155 A1 1/2014 Li et al.
2014/0011783 A1 1/2014 Li et al.
2014/0148421 A1 5/2014 Li et al.
2014/0194396 A1 7/2014 Li et al.
2014/0275131 A1 9/2014 Li et al.
2014/0315868 A1 10/2014 Li et al.
2014/0357606 A1 12/2014 Li et al.
2015/0038474 A1 2/2015 Li et al.
2015/0072965 A1 3/2015 Li et al.
2015/0080357 A1 3/2015 Li et al.
2015/0119370 A1 4/2015 Li et al.
2015/0197524 A1 7/2015 Li et al.
2015/0197528 A1 7/2015 Li et al.
2015/0219669 A1* 8/2015 Rouet .................. G01N 27/447
435/7.92
2015/0353556 A1 12/2015 Li et al.
2015/0374699 A1 12/2015 Wennogle et al.
2016/0031895 A1 2/2016 Li et al.
2016/0038494 A1* 2/2016 Wennogle .............. A61K 45/06
514/262.1
2016/0039835 A1 2/2016 Li et al.
2016/0083390 A1 3/2016 Li et al.
2017/0197974 A1 7/2017 Li et al.
2017/0226117 A1 8/2017 Li et al.

FOREIGN PATENT DOCUMENTS

EP 0 063 381 A1 10/1982
EP 0 095 289 A2 11/1983
EP 0 136 883 A2 4/1985
EP 0 201 188 A2 12/1986
EP 0 274 234 A2 7/1988
EP 0 358 398 A1 3/1990
EP 0 509 442 A1 10/1992
EP 0 519 738 A1 12/1992
EP 0 358 398 B1 3/1993
EP 0 599 444 A1 6/1994
EP 0 636 626 A1 2/1995
EP 0 690 070 A1 1/1996
EP 0 733 642 A1 9/1996
EP 0 599 444 B1 1/1998
EP 0 830 863 A1 3/1998
EP 0 911 333 A1 4/1999
EP 1 097 719 A1 5/2001
JP 53031694 A 3/1978
KR 10-1991-0006866 9/1991
WO WO 91/09840 7/1991
WO WO 91/19717 12/1991
WO WO 93/09101 5/1993
WO WO 94/15908 7/1994
WO WO 94/19351 9/1994
WO WO 96/14293 5/1996
WO WO 98/46606 10/1998
WO WO 98/52568 11/1998
WO WO 01/27113 4/2001
WO WO 02/074312 9/2002
WO WO 03/002567 1/2003
WO WO 03/020702 3/2003
WO WO 03/020724 3/2003
WO WO 03/042216 5/2003
WO WO 2006/133261 12/2006
WO WO 2007/143568 12/2007
WO WO 2007/143705 12/2007
WO WO 2008/063505 5/2008
WO WO 2008/070095 6/2008
WO WO 2009/073210 6/2009
WO WO 2009/075784 6/2009

(56) References Cited

FOREIGN PATENT DOCUMENTS

| | | |
|---|---|---|
| WO | WO 2009/137465 | 11/2009 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2010/065617 | 6/2010 |
| WO | WO 2010/098839 | 9/2010 |
| WO | WO 2011/016861 | 2/2011 |
| WO | WO 2011/043816 | 4/2011 |
| WO | WO 2011/133224 | 10/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/067913 | 5/2012 |
| WO | WO 2012/171016 | 12/2012 |
| WO | WO 2013/192556 | 12/2013 |
| WO | WO 2014/127331 | 8/2014 |
| WO | WO 2014/151409 | 9/2014 |
| WO | WO 2015/196186 | 12/2015 |
| WO | WO 2016/022825 | 2/2016 |
| WO | WO 2016/022836 | 2/2016 |
| WO | WO 2016/022893 | 2/2016 |
| WO | WO 2016/044667 | 3/2016 |

OTHER PUBLICATIONS

Aswar, M. et al., "Anti-Cataleptic Activity of Various Extracts of *Ocimum sanctum*," International Journal of Pharmaceutical Research and Development, 2010, 2 (6), 7 pages.

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender et al., "Selective up-regulation of PDE1B2 upon monocyte-to-macrophage differentiation," PNAS, 2005, 102(2):497-502.

Bender, A. et al., "Cyclic Nucleotide Phosphodiesterases: Molecular Regulation to Clinical Use," Pharmacological Reviews, 2006, 58 (3), 488-520.

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.

Broder, et al., "Chemotherapy and Cardiotoxicity", Rev. Cardiovasc. Med., 9(2), p. 75-83, (2008).

Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologie (Paris), 1986, 17 (3), 348-350.

Colombo, A. et al., "Managing Cardiotoxicity of Chemotherapy", *Current Treatment Options In Cardiovascular Medicine*, vol. 15, No. 4, pp. 410-424, (2013).

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.

Ennaceur, A. et al., "A New One-Trial Test for Neurobiological Studies of Memory in Rats. 1:Behavioral Data," Behavioural Brain Research, 1998, 31, 47-59.

Evgenov et al., "Inhibition of phosphodiesterase 1 augments the pulmonary vasodilator response to inhaled nitric oxide in awake lambs with acute pulmonary hypertension," Am J Physiol Lung Cell Mol Physiol, 2006, 290:L723-L729.

Fienberg, A. et al., "DARPP-32: Regulator of the Efficacy of Dopaminergic Neurotransmission," Science, 1998, 281, 838-842.

Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

Gelbin, M. et al., "Ketene-S,N-acetals as Synthons for Heterocycles, New Synthesis of Pyrimidinones," Journal Für Praktische Chemie, 1987, 329 (5), 753-766.

Ghorab, M.M. et al., Synthesis, anticancer and radioprotective activities of some new pyrazolo[3,4-d]pyrimidines containing amino acid moieties, Arzneimittel Forschung, 2009, vol. 59, No. 2, pp. 96-103.

Giachini et al., "CHBPR: Decreased cGMP level contributes to increased contraction in arteries from hypertensive rats: role of PDE1", Hypertension, 2011, 57(3): 655-663.

Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.

Greengard, P. et al., "Beyond the Dopamine Receptor: The DARPP-32/Protein Phosphatase-1 Cascade," Neuron, 1999, 23, 435-447.

Gulyas, B. et al., "PET studies on the brain uptake and regional distribution of [11C]vinpocetine in human subjects," Acta Neurologica Scandinavica, 2002, 106: 325-332.

Hall et al., "Autoradiographic evaluation of [11C]vinpocetine Binding in the Human Postmortem Brain," Acta Biologica Hungarica, 2002, 53(1-2): 59-66.

Han, P. et al., "The Calcium/Calmodulin-dependent Phosphodiesterase PDEIC Down-regulates Glucose-induced Insulin Secretion," The Journal of Biological Chemistry, 1999, 274 (32), 22337-22344.

Hashimoto, T. et al. "Acute Enhancement of Cardiac Function by Phosphodiesterase Type 1 Inhibition: A Translational Study in the Dog and Rabbit," Circulation, 2018, 138(18):1974-1987.

Hulley, P. et al., "Cyclic AMP Promotes the Survival of Dopaminergic Neurons in vitro and Protects Them from the Toxic Effects of $MPP^+$," Journal of Neural Transmission [Supplemental], 1995, 46, 217-228.

International Search Report for International Application No. PCT/US2014/016741, prepared by the International Searching Authority, date mailed: May 14, 2014, 3 pages.

International Search Report for International Application No. PCT/US2015/044164, prepared by the International Searching Authority, date mailed: Oct. 29, 2015, 3 pages.

Jiang, M. et al., "Chemoenzymatic Asymmetric Total Synthesis of Phosphodiesterase Inhibitors: Preparation of a Polycyclic Pyrazolo[3,4-

(56) References Cited

OTHER PUBLICATIONS d]pyrimidine from an Acylnitroso Diels-Alder Cycloadduct-Derived Aminocyclopentenol," Journal of Organic Chemistry, 2005, 70, 2824-2827.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Kakkar et al., "Calmodulin-dependent cyclic nucleotide phosphodiesterase in an experimental rat model of cardiac ischemia-reperfusion." Can J Physiol Pharmacol, 2002, 80(1):59-66 (Abstract Only).
Kim et al., "Upregulation of Phosphodiesterase 1A1 Expression Is Associated With the Development of Nitrate Tolerance." Circulation, 2001, 104(19):2338-43.
Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi: 10.1186/1471-2202-13-132, 15 pages.
Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.
Knight et al., "PDE1C deficiency antagonizes pathological cardiac remodeling and dysfunction," PNAS, E7116-E7125 (2016).
Kotera et al., "Recent progress in cyclic nucleotide phosphodiesterase research: isozymes, functions, and inhibitors," Folia Pharmacol. Jpn., 2005, 126(2):121-127.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Laursen, et al., "Novel Selective PDE Type 1 Inhibitors Cause Vasodilation and Lower Blood Pressure in Rats", British Journal of Pharmacology, vol. 174, No. 15, p. 2563-2575, (2017).
Leroy, J. et al. "Inhibit a Phosphodiesterase to Treat Heart Failure? This is the One," Circulation, 2018, 138:2003-2006.
Li et al., "Discovery of Potent and Selective Inhibitors of Phosphodiesterase 1 for the Treatment of Cognitive Impairment Associated with Neurodegenerative and Neuropsychiatric Diseases," J. Med. Chem., vol. 59, No. 3, pp. 1149-1164, (2016).
Lundqvist, T. et al., "Exploitation of Structural and Regulatory Diversity in Glutamate Racemases," Nature, 2007, 447, 817-822.
Lourenco et al, "Characterization of R-[11C]rolipram for PET imaging of phosphodiesterase-4; in vivo binding, metabolism, and dosimetry studies in rats," Nuclear Medicine and Biology, 2001, 28: 347-358.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Miller et al., "Role of Ca2+/calmodulin-stimulated cyclic nucleotide phosphodiesterase 1 in mediating cardiomyocyte hypertrophy." Circ Res 2009, 105(10):956-64.
Miller et al., "Cyclic nucleotide phosphodiesterase 1A: a key regulator of cardiac fibroblast activation and extracellular matrix remodeling in the heart," Basic Res Cardiol., 2011, 106(6): 1023-1039.
Mokni et al., "Concerted Regulation of cGMP and cAMP Phosphodiesterases in Early Cardiac Hypertrophy Induced by Angiotensin II," PLoS One., 2010 5(12):e14227, 15 pages.
Murray, F., et al., "Expression and activity of cAMP phosphodiesterase isoforms in pulmonary artery smooth muscle cells from patients with pulmonary hypertension: role for PDE1," Am. J. Physiol. Lunr:1 Cell Mol. Physiol. 2007, 292, pp. L294-L303.
Murray, T. et al., "LY503430, A Novel a-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.
Park, E, et al., "Traumatic Brain Injury: Can the Consequences Be Stopped?" CMAJ, 2008, 178 (9), 1163-1170.
Patani et al., "Bioisosterism: A Rational Approach in Drug Design", Chem. Rev. 1996, 96, 3147-3176.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rickles et al., "Adenosine A2A receptor agonists and PDE inhibitors: a synergistic multitarget mechanism discovered through systematic combination screening in B-cell malignancies," Blood, 116(4):593-602 (2010).
Rosa, et al., "Update on cardiotoxicity of anti-cancer treatments", *European Journal of Clinical Investigation*, 46(3), pp. 264-284, (2016).
Rybalkin, S. et al., "Cyclic GMP Phosphodiesterases and Regulation of Smooth Muscle Function," Circulation Research, 2003, 93, 280-291.
Rybalkin et al., "Cyclic Nucleotide Phosphodiesterase 1C Promotes Human Arterial Smooth Muscle Cell Proliferation," Circulation Research, 2002, 90(2):151-7.
Schermuly et al., "Phosphodiesterase 1 Upregulation in Pulmonary Arterial Hypertension," Circulation, 2007, 115:2331-2339.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Silva, "Advances in Prodrug Design," Mini-Reviews in Medicinal Chemistry, 2005, 5:893-914.

(56) References Cited

OTHER PUBLICATIONS

Snyder, G.L. et al., "Preclinical Profile of ITI-214, an Inhibitor of Phosphodiesterase 1, for Enhancement of Memory Performance in Rats," Psychopharmacology, 2016, 233, 3113-3124, DOI: 10.1007/s00213-016-4346-2.

Takimoto, E., "Controlling Myocyte cGMP: Phosphodiesterase 1 Joins the Fray," Circ Res., 2009, 105(10):931-933.

"The Diagnosis and Management of Duchenne Muscular-Dystrophy: A Guide for Families," Treat-NMD, First Issue, 2011, [retrieved on Mar. 6, 2018], Retrieved from the Internet: <URL:: http://www.treat-nmd.eu/downloads/file/standardsofcare/dmd/japan/DMDweb03_02pass.pdf>.

Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.

Ungerstedt, U. et al., "Quantitative Recording of Rotational Behavior in Rats After 6-Hydroxy-dopamine Lesions of the Nigrostriatal Dopamine System," Brain Research, 1970, 24, 485-493.

Ungerstedt, U., "Stereotaxic Mapping of the Monoamine Pathways in the Rat Brain," Acta Physiologica Scandinavica, Supplementum 367, 1971, 1-48.

Vas, A. et al. "Clinical and non-clinical investigations using positron emission tomography, near infrared spectroscopy and transcranial Doppler methods on the neuroprotective drug vinpocetine: A summary of evidences," Journal of the Neurological Sciences, 2002, 203-204: 259-262.

Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.

Wallis et al., "Tissue distribution of phosphodiesterase families and the effects of sildenafil on tissue cyclic nucleotides, platelet function, and the contractile responses of trabeculae carneae and aortic rings in vitro.", Am J Cardiol., 1999, 83(5A): 3C-12C.

Wermuth, CG, ed., "Molecular Variations based on isosteric replacements" The Practice of Chemistry, Technomics, Inc., Aug. 1998, vol. 1, Section 13, pp. 235-271.

Willerson et al., "Inflammation as a Cardiovascular Risk Factor," Circulation, 2004, 109: II-2-II-10.

Wolff, Burger's Medicinal Chemistry and Drug Discovery, Fifth Edition, vol. I: Principles and Practice, John Wiley & Sons, New York, 1995, 975-977.

Xia et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.

Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.

Zhang et al., "Phosphodiesterases and cardiac cGMP: evolving roles and controversies," Trends in Pharmacological Sciences, 2011, 32(6): 360-365.

Zhang, et al., "Multiprotein Complex With TRPC (Transient Receptor Potential-Canonical) Channel, PDEIC (Phosphodiesterase IC), and A2R (Adenosine A2 Receptor) Plays a Critical Role in Regulating Cardiomyocyte cAMP and Survival", Circulation, vol. 138, p. 1988-2002, (2018).

Kass, D., "Cardiac Role of Cyclic-GMP Hydrolyzing Phosphodiesterase Type 5: From Experimental Models to Clinical Trials" Current Heart Failure Reports, Current Science, Inc. vol. 9, No. 3, 2012, pp. 192-199.

* cited by examiner

USES

CROSS-REFERENCE TO RELATED APPLICATIONS

This application is a divisional of U.S. patent application Ser. No. 16/892,206, filed Jun. 3, 2020, which is a Continuation-in-Part of International Application No. PCT/US19/16128, filed Jan. 31, 2019, which claims priority to U.S. Provisional Patent Application No. 61/700,126, filed Jul. 18, 2018; U.S. Provisional Patent Application No. 62/683,431, filed Jun. 11, 2018; and 62/624,705, filed Jan. 31, 2018, and the contents of which are hereby incorporated by reference in their entirety.

FIELD OF THE DISCLOSURE

This disclosure relates to the administration of inhibitors of phosphodiesterase 1 (PDE1) to potentiate or enhance adenosine $A_2$ signaling, for example in cardiac tissues, e.g., to enhance cardiac function, to enhance the effects of adenosine $A_2$ agonists, including endogenous adenosine, and to treat heart failure and diseases or disorders involving impaired or inadequate adenosine $A_2$ mediated pathways.

BACKGROUND

From a therapeutic standpoint, PDEs are of particular therapeutic interest, as their structure is amenable to specific and potent small molecule inhibitors, and cell-specific expression provides selective organ targeting. There are 11 identified families of PDE totaling over 100 isoforms. PDE4, PDE7, and PDE8 are highly selective for cAMP, and PDE5, PDE6, and PDE9 for cGMP. The remaining PDEs hydrolyze both, with selectivity depending on biological conditions, and in some instances isoforms. The heart and/or myocytes express mRNA for all but PDE6, and functional roles have been identified for PDE1, PDE2, PDE3, PDE4, PDE5, PDE8, and PDE9. Inhibitors of several of these PDEs have been translated to humans in the form of FDA approved medications.

PDE1 is expressed as one of three isoforms, with PDE1A and PDE1C found in the heart, and PDE1B primarily in the brain. PDE1A is more selective for cGMP ($K_m$ 33-fold higher than for cAMP), whereas PDE1C has similar affinities for both cyclic nucleotides. PDE1 is constitutively expressed in the heart and hydrolyzes both cyclic AMP and/or cGMP. However, very little is known about its role in cardiovascular regulation. Rodent hearts mostly expresses the highly cGMP-favoring PDE1A isoform in heart tissue, whereas humans predominantly express PDE1C in heart tissue, with effects on both cGMP and cAMP. In mice, non-selective PDE1 inhibition has been shown to attenuate cardiac hypertrophy and fibrosis, with enhancement of cGMP. However, no study has yet examined cardiovascular effects of PDE1 inhibition in mammals, such as humans, that predominantly express PDE1C in the heart, nor has the impact of PDE1 inhibition been studied in combination with relevant treatments, such as after beta-adrenergic or adenosine stimulation/blockade.

Adenosine is an endogenous purine nucleoside that modulates many physiological processes. Cellular signaling by adenosine occurs through four known adenosine receptor subtypes ($A_1$, $A_{2A}$, $A_{2B}$, and $A_3$). Extracellular adenosine concentrations from normal cells are approximately 300 nM; however, in response to cellular damage (e.g. in inflammatory or ischemic tissue), these concentrations are quickly elevated (600-1,200 nM). Adenosine has a cytoprotective activity, helping to prevent or limit tissue damage during instances of hypoxia, ischemia, and seizure activity. The adenosine receptor subtypes ($A_1$, $A_{2A}$, $A_{2B}$, and $A_3$) are G-protein-coupled receptors. The four receptor subtypes are further classified based on their ability to either stimulate or inhibit adenylate cyclase activity. The $A_1$ and $A_3$ receptors couple to inhibitory G proteins, and decrease cAMP levels, while the $A_2$ adenosine receptors couple to $G_s$, which stimulates adenylate cyclase activity and enhances cAMP levels. Adenosine is used as a therapeutic, for example, to evaluate or treat arrhythmias such as supraventricular tachycardia (SVT). However, adenosine or non-selective or partially selective adenosine agonists may cause serious side effects, such as bradycardia, a decrease in blood pressure and a decrease in cardiac output, which side effects seem to be primarily related to stimulation of adenosine $A_1$ receptors, which leads to antiadrenergic effects. Selective adenosine $A_{2B}$ receptor agonists are in development, which may be useful to reduce damage from ischemia (lack of oxygen due to blocked blood supply) and to treat acute heart, lung and brain injury, but they are not yet available commercially.

Modulation of adenosine-related pathways could provide a wide range of therapeutic effects. Activation of the $A_{2A}$ adenosine receptor has been shown to have cardioprotective effects. Many commonly prescribed anti-cancer drugs are known to have cardiotoxic effects. For example, cytostatic antibiotics of the anthracycline class are the best known of the chemotherapeutic agents that cause cardiotoxicity. Other chemotherapeutics, like cyclophosphamide, ifosfamide, cisplatin, carmustine, busulfan, chlormethine and mitomycin, have also been associated with cardiotoxicity. This cardiotoxicity could lead to a variety of heart-related conditions, including mild blood pressure changes, thrombosis, electrocardiographic changes, arrhythmias, myocarditis, pericarditis, myocardial infarction, cardiomyopathy, cardiac failure (left ventricular failure) and congestive heart failure.

Heart failure (HF) affects an estimated 30-50 million patients worldwide. Despite recent therapeutic advances, its prevalence is increasing, partly due to a fall in mortality, but also from higher rates of major co-morbidities such as obesity, diabetes, and age. Currently, there is a largely unmet need for an effective way of treating cardiovascular disease and disorders (e.g. congestive heart failure), and diseases and disorders which may result in cardiac dysfunction or cardiomyopathy (e.g., Duchenne Muscular Dystrophy).

Improved therapeutic compositions and methods for the treatment of cardiac conditions and dysfunction are urgently required.

SUMMARY

A major component of cardiac dysfunction in HF resides in second messenger signaling defects coupled to cyclic 3', 5'-cyclic adenosine and guanosine monophosphate (cAMP, cGMP) that limit functional reserve. Cyclic AMP stimulates protein kinase A (PKA) and exchange protein activated by cAMP (EPAC), acutely enhancing excitation-contraction coupling and sarcomere function. Cyclic GMP acts as a brake on this signaling by activating protein kinase G. Both cyclic nucleotides have relevant vascular and fibroblast activity, reducing vessel tone, altering permeability and proliferation, and suppressing fibrosis. The synthesis of cAMP is provided by adenylyl cyclase and that of cGMP by guanylyl cyclases. Degradation (hydrolysis) of these cyclic nucleotides is accomplished by cyclic nucleotide phosphodiesterases (PDEs). PDE1 is believed to be up-regulated in chronic disease conditions such as atherosclerosis, cardiac pressure-load stress and heart failure, as well as in response to long-term exposure to nitrates. PDE1 inhibitors, e.g., as described herein, are thus able to modulate cAMP/PKA and cGMP/PKG mediated pathways in cardiac, vascular, and lung tissues, where PDE1 is expressed.

We have found that, in mammals where PDE1C is the predominant PDE1 isoform in cardiac tissue, PDE1 inhibition has acute positive inotropic, lusitropic, and arterial vasodilatory effects, which are dependent on $A_{2B}$-adenosine signaling but independent of beta-adrenergic receptor signaling. These effects are seen in both healthy and failing hearts. Studies have thus far confirmed only that $A_{2B}R$ couples to PDE3B regulation in hepatocytes and PDE4D in pulmonary airway epithelial cells, so the present disclosure and data linking $A_{2B}R$ signalling to PDE1 are novel and quite unexpected.

While PDE1 inhibitors by themselves have relatively little impact on unstimulated cardiac tissue, when the tissue is stimulated by endogenous adenosine and/or by adenosine $A_2$ agonists, PDE1 inhibitors can potentiate and enhance $A_{2B}R$ signaling by inhibiting the degradation of cyclic nucleotides (believed in this pathway to be primarily cAMP), thereby enhancing and prolonging the inotropic, lusitropic, and arterial vasodilatory effects of adenosine $A_{2B}$ stimulation, and consequently increasing cardiac output without altering arterial systolic pressure, even in failing hearts. Enhancing adenosine PDE1 inhibitors are therefore potentially useful to treat various cardiovascular diseases and disorders, such as angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, an inflammatory disease or disorder, fibrosis, cardiac hypertrophy, vascular remodeling, a connective tissue disease or disorder (e.g., Marfan Syndrome), chronic heart failure, acute heart failure, myocardial ischemia, myocardial hypoxia, reperfusion injury, left ventricular dysfunctions (e.g., myocardial infarction, ventricular expansion), or vascular leakage (i.e., consequent to hypoxia), muscular dystrophy (e.g., Duchenne muscular dystrophy), and amyotrophic lateral sclerosis, or any of these disorders characterized by inotropic or lusitropic dysfunction (e.g., cardiac hypertrophy characterized by inotropic dysfunction).

Moreover, by selectively enhancing the effects of adenosine $A_2$ signaling, PDE1 inhibitors can be used to in combination with adenosine or other non-selective or partially selective adenosine receptor agonist, to reduce effective dose of the adenosine receptor agonist, to provide an adenosine $A_2$-selective, e.g., adenosine $A_{2B}$-selective, therapy, and to minimize undesirable side effects, e.g., side effects related to adenosine $A_1$ receptor activity, such as bradycardia, decrease in blood pressure and decrease in cardiac output. For example, in some embodiments, the disclosure provides methods of reducing side effects of adenosine or other non-selective or partially selective adenosine receptor agonists, by administering the adenosine agonist at a low dose, in combination with a PDE1 inhibitor, wherein the dose of adenosine agonist is too low to trigger side effects, e.g., due to adenosine $A_1$ receptor activity, but effective in combination with a PDE1 inhibitor to provide adenosine $A_2$ receptor stimulation.

Thus, in another embodiment, the PDE1 inhibitor (e.g., a PDE1 inhibitor of Formula I', Ia, II', III', IV', V, and/or VI as herein described) may be administered for the treatment or prophylaxis of a disease or condition characterized by adenosine $A_2$ dysfunction or which would benefit from adenosine $A_2$ stimulation, comprising administration of an effective amount of a PDE1 inhibitor to a patient in need thereof. For example, the disease or condition characterized by adenosine $A_2$ dysfunction may be chronic heart failure; acute heart failure; heart failure consequent to myocardial infarction; inflammatory disorders (e.g., colitis, inflammatory bowel syndrome, acute vascular inflammation, acute intestinal inflammation, ulcerative inflammation); sickle-cell disease; multiple sclerosis; stroke; traumatic brain injury; Alzheimer's disease; fibrosis; hypoxia; ischemia; reperfusion injury; left ventricular dysfunction (e.g., myocardial infarction, ventricular expansion); caffeine withdrawals; acute lung injury; vascular leakage consequent to hypoxia; myocardial ischemia; sleep disorders; sepsis; irritable bowel syndrome; skin pressure; ulcers; or wound healing.

In some embodiments, the present disclosure also provides for a combination therapy comprising a PDE1 inhibitor and an additional therapeutic agent selected from adenosine $A_2$ agonist; a beta-adrenergic receptor antagonist (i.e., a beta-blocker); an ACE inhibitor; an angiotensin receptor blocker (ARBs); antihyperlipoproteinemic agent; an antiarteriosclerotic agent; an antithrombotic/fibrinolytic agent; a blood coagulant; an antiarrhythmic agent; an antihypertensive agent; a vasopressor; a treatment agent for congestive heart failure; an antianginal agent; an antibacterial agent; neprilysin inhibitors or a combination thereof.

DETAILED DESCRIPTION OF THE DISCLOSURE

Compounds for Use in the Methods of the Disclosure

In certain embodiments, the present disclosure provides that the PDE1 inhibitors for use in the methods of treatment and prophylaxis described herein are selected from the PDE1 inhibitors described in the Applicant's own publications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, WO 2012/171016, WO 2013/192556, WO 2014/151409, WO 2015/196186, WO 2016/022825, WO 2016022836, WO 2016/022893, WO 2016/044667, U.S. Pat. No. 9,546,175, the entire contents of each of which are incorporated herein by reference in their entireties.

In one embodiment the invention provides that the PDE1 inhibitors for use in the methods of treatment and prophylaxis described herein are compounds of Formula I':

Formula I'

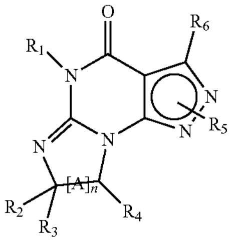

wherein (i) $R_1$ is H or $C_{1-4}$ alkyl (e.g., methyl);

(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or $R_2$ is H and $R_3$ and $R_4$ together form a di-, tri- or tetramethylene bridge (pref wherein the $R_3$ and $R_4$ together have the cis configuration, e.g., where the carbons carrying $R_3$ and $R_4$ have the R and S configurations, respectively);

(iii) $R_5$ is a substituted heteroarylalkyl, e.g., substituted with haloalkyl;

or $R_5$ is attached to one of the nitrogens on the pyrazolo portion of Formula I' and is a moiety of Formula A Formula A'

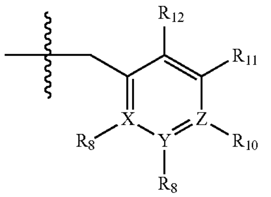

wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heteroarylamino, N,N-dialkylamino, N,N-diarylamino, or N-aryl-N-(arylalkyl)amino (e.g., N-phenyl-N-(1,1'-biphen-4-ylmethyl)amino); and (v) n=0 or 1;

(vi) when n=1, A is $-C(R_{13}R_{14})-$ wherein $R_{13}$ and $R_{14}$, are, independently, H or $C_{1-4}$ alkyl, aryl, heteroaryl, (optionally hetero)arylalkoxy or (optionally hetero)arylalkyl;

in free, salt or prodrug form, including its enantiomers, diastereoisomers and racemates.

In another embodiment the invention provides that the PDE1 inhibitors for use in the methods as described herein are Formula 1a:

Formula Ia

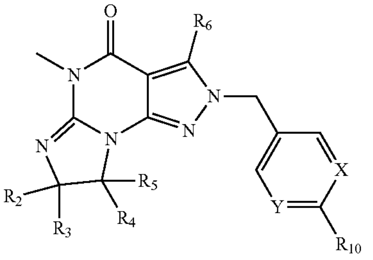

wherein (i) $R_2$ and $R_5$ are independently H or hydroxy and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ and $R_5$ are each H; or $R_2$, $R_4$ and $R_5$ are H and $R_3$ is isopropyl [pref the carbon carrying $R_3$ having the R configuration];

(ii) $R_6$ is (optionally halo- or hydroxy-substituted) phenylamino, (optionally halo- or hydroxy-substituted) benzylamino, $C_{1-4}$alkyl, or $C_{1-4}$alkyl sulfide; for example, phenylamino or 4-fluorophenylamino;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and X and Y are independently C or N, in free, pharmaceutically acceptable salt or prodrug form, including its enantiomers, diastereoisomers and racemates.

In another embodiment the invention provides that the PDE1 inhibitors for use in the methods of treatment and prophylaxis described herein are compounds of Formula II':

Formula II'

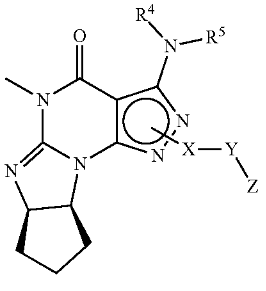

(i) X is $C_{1-6}$alkylene (e.g., methylene, ethylene or prop-2-yn-1-ylene);

(ii) Y is a single bond, alkynylene (e.g., $-C\equiv C-$), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), C(O) $R^1$, $N(R^2)(R^3)$, or $C_{3-7}$cycloalkyl optionally containing at least one atom selected from a group consisting of N or O (e.g., cyclopentyl, cyclohexyl, tetrahydro-2H-pyran-4-yl, or morpholinyl);

(iv) $R^1$ is $C_{1-6}$alkyl, halo$C_{1-6}$alkyl, OH or O$C_{1-6}$alkyl (e.g., $OCH_3$);

(v) $R^2$ and $R^3$ are independently H or $C_{1-6}$alkyl;

(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;

(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In yet another embodiment the invention provides that the PDE1 inhibitors for use in the methods of treatment and prophylaxis described herein are Formula III':

Formula III'

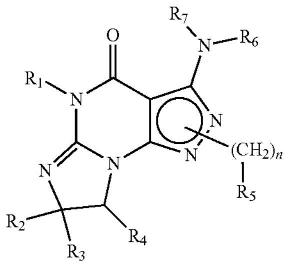

wherein (i) R1 is H or $C_{1-4}$ alkyl (e.g., methyl or ethyl);

(ii) $R_2$ and $R_3$ are independently H or $C_{1-6}$ alkyl (e.g., methyl or ethyl);

(iii) $R_4$ is H or $C_{1-4}$ alkyl (e.g., methyl or ethyl);

(iv) $R_5$ is aryl (e.g., phenyl) optionally substituted with one or more groups independently selected from —C(═O)—$C_{1-6}$ alkyl (e.g., —C(═O)—$CH_3$) and $C_{1-6}$-hydroxyalkyl (e.g., 1-hydroxyethyl);

(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and (vi) n is 1, 2, 3, or 4, in free or salt form.

In yet another embodiment the invention provides that the PDE1 inhibitors for use in the methods of treatment and prophylaxis described herein are Formula IV':

Formula IV'

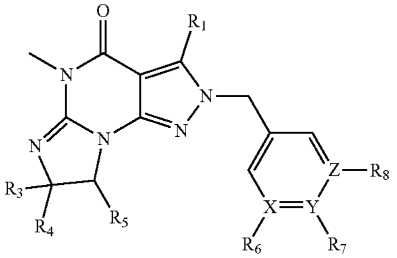

in free or salt form, wherein (i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;

(ii) X, Y and Z are, independently, N or C;

(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively), (iv) $R_6$, $R_7$ and $R_8$ are independently:

H, $C_{1-4}$alkyl (e.g., methyl), pyrid-2-yl substituted with hydroxy, or

—$S(O)_2$—$NH_2$;

(v) Provided that when X, Y and/or Z are N, then $R_6$, $R_7$ and/or $R_8$, respectively, are not present; and when X, Y and Z are all C, then at least one of $R_6$, $R_7$ or $R_8$ is —$S(O)_2$—$NH_2$ or pyrid-2-yl substituted with hydroxy.

In another embodiment the invention provides that the PDE1 inhibitors for use in the methods as described herein are Formula V:

Formula V

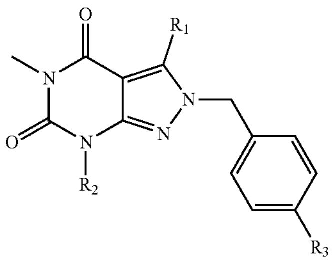

wherein (i) $R_1$ is —NH($R_4$), wherein $R_4$ is phenyl optionally substituted with halo (e.g., fluoro), for example, 4-fluorophenyl;

(ii) $R_2$ is H or $C_{1-6}$alkyl (e.g., methyl, isobutyl or neopentyl);

(iii) $R_3$ is —$SO_2NH_2$ or —COOH;

in free or salt form.

In another embodiment the invention provides that the PDE1 inhibitors for use in the methods as described herein are Formula VI:

Formula VI

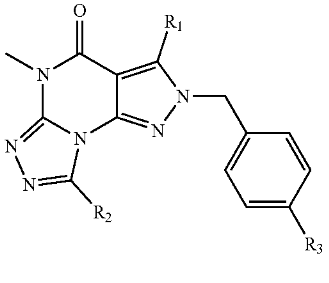

wherein (i) $R_1$ is —NH($R_4$), wherein $R_4$ is phenyl optionally substituted with halo (e.g., fluoro), for example, 4-fluorophenyl;

(ii) $R_2$ is H or $C_{1-6}$alkyl (e.g., methyl or ethyl);

(iii) $R_3$ is H, halogen (e.g., bromo), $C_{1-6}$alkyl (e.g., methyl), aryl optionally substituted with halogen (e.g., 4-fluorophenyl), heteroaryl optionally substituted with halogen (e.g., 6-fluoropyrid-2-yl or pyrid-2-yl), or acyl (e.g., acetyl), in free or salt form.

In one embodiment, the present disclosure provides for administration of a PDE1 inhibitor for use in the methods described herein (e.g., a compound according to Formulas I', Ia, II', III', IV', V, and/or VI), wherein the inhibitor is a compound according to the following:
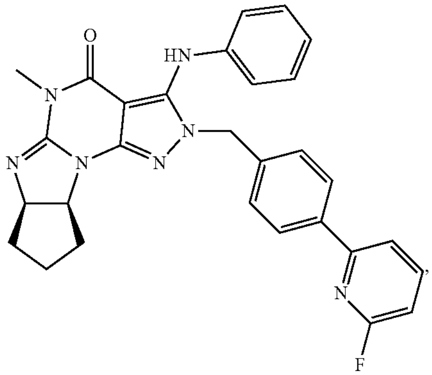
,
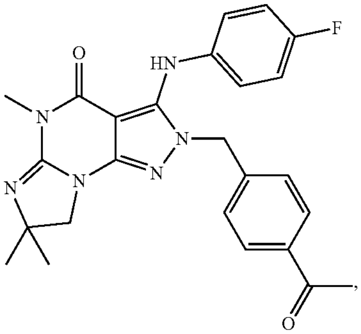
,
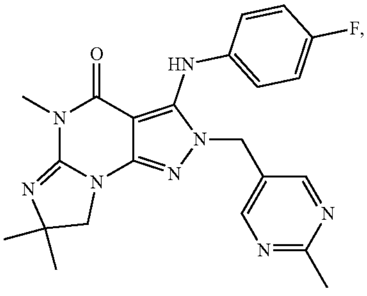
,
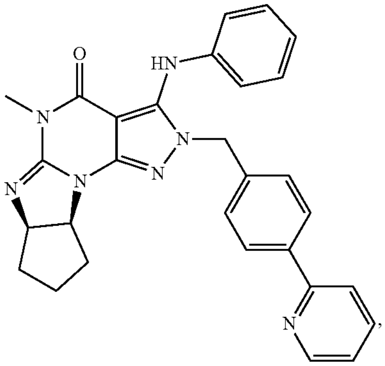
,
-continued
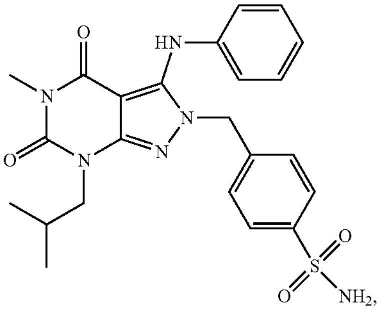
,
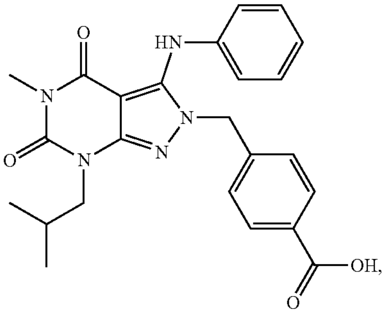
,
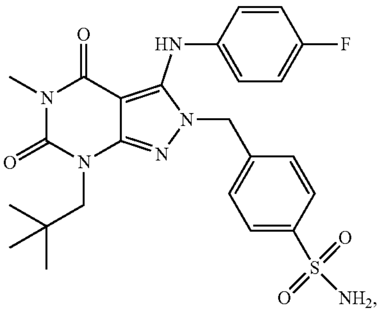
,
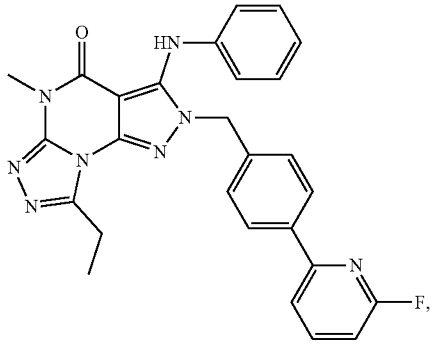
,
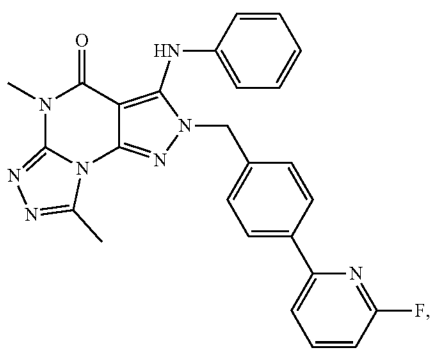
, -continued
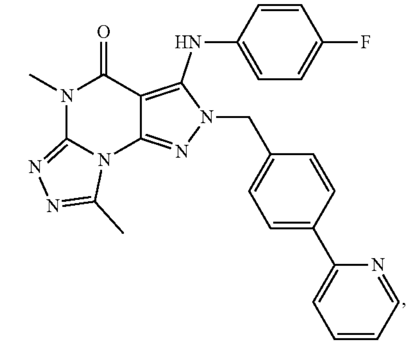
,
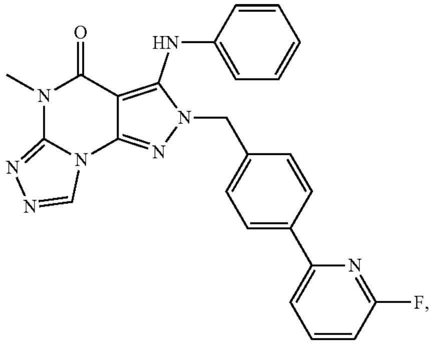
,
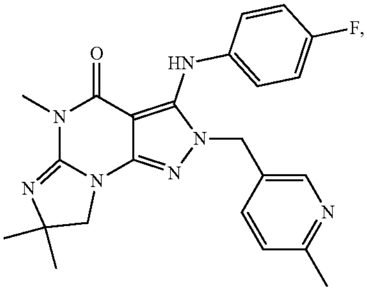
,
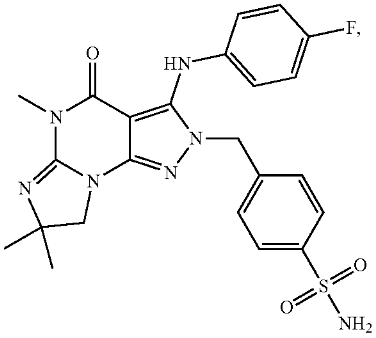
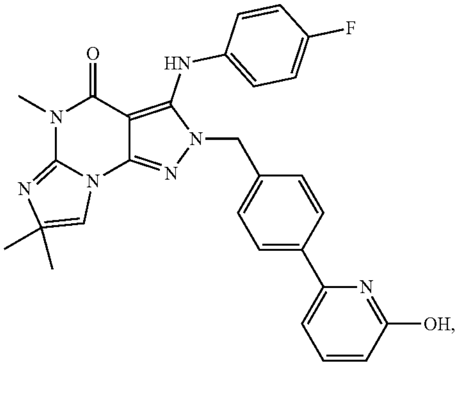
,
-continued
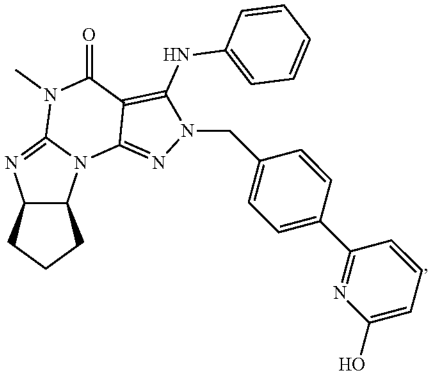
,
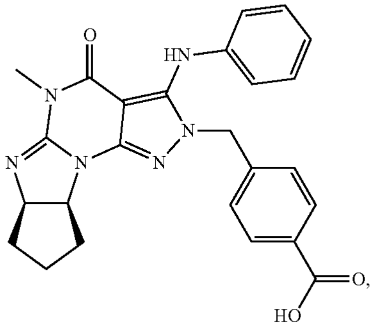
,
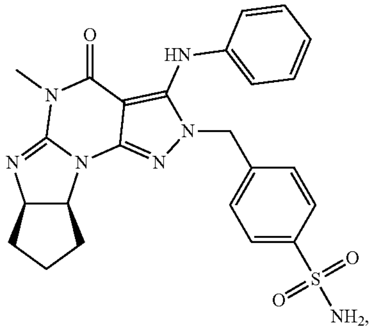
,
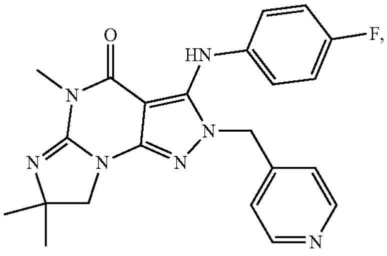
, or
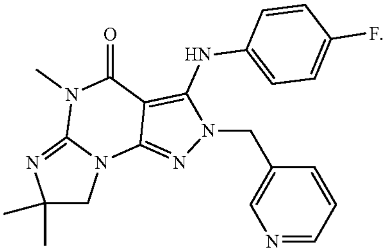
.
In one embodiment the invention provides administration of a PDE1 inhibitor for treatment or prophylaxis of inflammation or an inflammatory related disease or disorder, wherein the inhibitor is a compound according to the following:

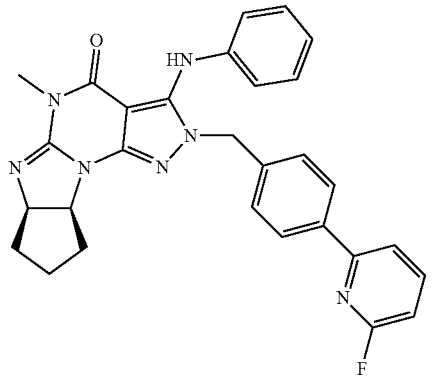 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

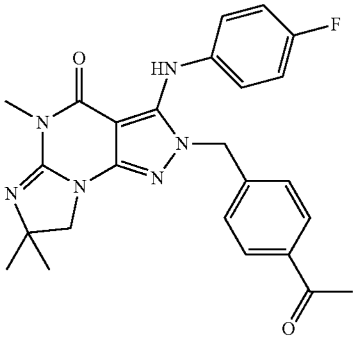 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

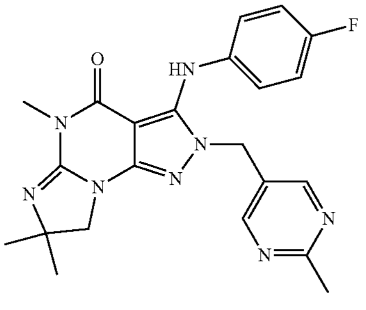 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

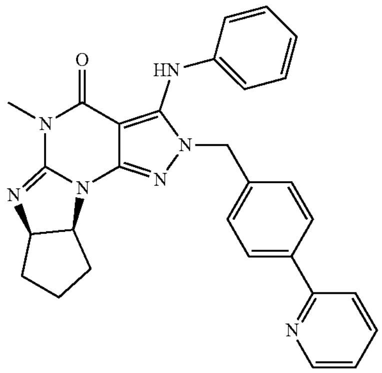 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

In one embodiment, selective PDE1 inhibitors of the any of the preceding formulae (e.g., Formula I', Ia, II', III', IV', V and/or VI) are compounds that inhibit phosphodiesterase-mediated (e.g., PDE1-mediated, especially PDE1B-mediated) hydrolysis of cGMP, e.g., the preferred compounds have an $IC_{50}$ of less than 1p M, preferably less than 500 nM, preferably less than 50 nM, and preferably less than 5 nM in an immobilized-metal affinity particle reagent PDE assay, in free or salt form.

In other embodiments, the invention provides administration of a PDE1 inhibitor for treatment of a condition selected from a cancer or tumor; for inhibiting the proliferation, migration and/or invasion of tumorous cells; and/or for treating a glioma, wherein the inhibitor is a compound according to the following:

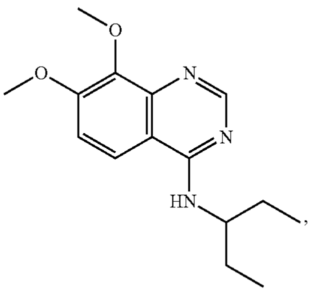

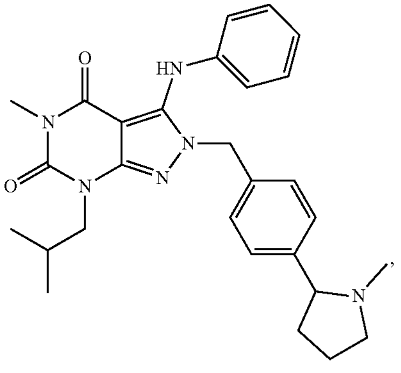

-continued

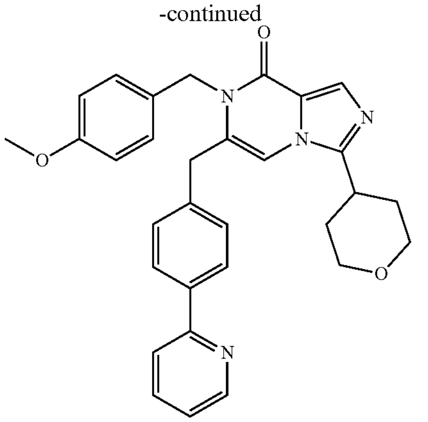

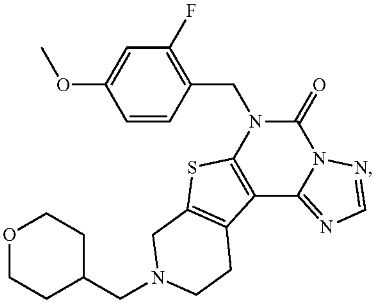

or

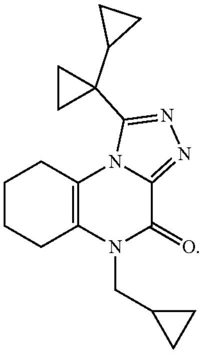

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; U.S. Publication 2017/0291901A1; International Publication WO2018/115067; U.S. Publication 2018/0179200A; U.S. Publication US20160318910A1; U.S. Pat. No. 9,868,741; International Publication WO2017/139186A1; International Application WO2016/040083; U.S. Publication 2017/0240532; International Publication WO 2016033776A1; U.S. Publication 2017/0233373; International Publication WO2015130568; International Publication WO2014159012; U.S. Pat. Nos. 9,034,864; 9,266,859; International Publication WO2009085917; U.S. Pat. No. 8,084,261; International Publication WO2018039052; U.S. Publication US20180062729; and International Publication WO2019027783 each of which are incorporated by reference in their entirety. In any situation in which the statements of any documents incorporated by reference contradict or are incompatible with any statements made in the present disclosure, the statements of the present disclosure shall be understood as controlling.

Still further examples of PDE1 inhibitors and suitable methods of use are disclosed in International Application PCT/US2019/033941 and U.S. Provisional Application 62/789,499, both of which are incorporated by reference herein.

If not otherwise specified or clear from context, the following terms herein have the following meanings:

(a) "Selective PDE1 inhibitor" as used herein refers to a PDE1 inhibitor with at least 100-fold selectivity for PDE1 inhibition over inhibition of any other PDE isoform.

(b) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(c) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(d) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(e) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(f) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(g) For ease of reference, the atoms on the pyrazolo-pyrimidine core of the Compounds of the Disclosure are numbered in accordance with the numbering depicted in Formula I, unless otherwise noted.

(h) Wherein E is phenylene, the numbering is as follows:

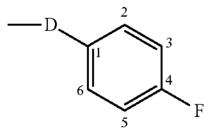

(i) It is intended that wherein the substituents end in "ene", for example, alkylene, phenylene or arylalkylene, said substituents are intended to bridge or be connected to two other substituents. Therefore, methylene is intended to be $—CH_2—$ and phenylene intended to be $—C_6H_4—$ and arylalkylene is intended to be $—C_6H_4—CH_2—$ or $—CH_2—C_6H_4—$.

(j) The Compounds of the Disclosure are intended to be numbered as follows:

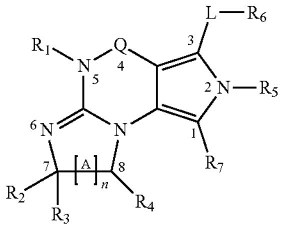

or

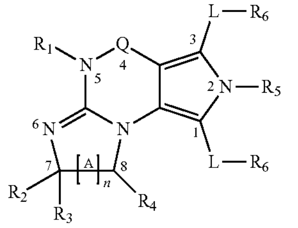

Compounds of the Disclosure, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula III, or Compound of Formula IV as described herein, may exist in free or salt form, e.g., as acid addition salts.

Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Disclosure contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the disclosure further provides a pharmaceutical composition comprising a Compound of the Disclosure, in free or pharmaceutically acceptable salt form, in admixture with a pharmaceutically acceptable carrier.

In another embodiment, the disclosure further provides a pharmaceutical composition comprising a Compound of the Disclosure, in free, pharmaceutically acceptable salt or prodrug form, in admixture with a pharmaceutically acceptable carrier.

In some embodiments, the Compounds of the Disclosure may be modified to affect their rate of metabolism, e.g., to increase half-life in vivo. In some embodiments, the compounds may be deuterated or fluorinated to reduce the rate of metabolism of the compounds disclosed herein.

In still another further embodiment, the compounds disclosed herein may be in the form of a pharmaceutical composition, for example for oral administration, e.g., in the form of tablets or capsules, or for parenteral administration. In some embodiments, the compounds are provided in the form of a long acting depot composition for administration by injection to provide sustained release. In some embodiments, the solid drug for oral administration or as a depot may be in a suitable polymer matrix to provide delayed release of the active compound.

Methods of Making Compounds of the Disclosure

The Compounds of the Disclosure and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. Starting materials and methods of making Compounds of the Disclosure are described in the patent applications cited and incorporated by reference above.

The Compounds of the Disclosure include their enantiomers, diastereoisomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the disclosure is the $^{11}C$ isotope. These radio isotopes are useful for radio-imaging and/or pharmacokinetic studies of the compounds of the disclosure.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations

BuLi=n-butyllithium
$Bu^tOH$=tert-butyl alcohol,
CAN=ammonium cerium (IV) nitrate,
DIPEA=diisopropylethylamine,
DMF=N,N-dimethylforamide,
DMSO=dimethyl sulfoxide,
$Et_2O$=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
$NaHCO_3$=sodium bicarbonate,
$NH_4OH$=ammonium hydroxide,
$Pd_2(dba)_3$=tris[dibenzylideneacetone]dipalladium(0)
PMB=p-methoxybenzyl,
$POCl_3$=phosphorous oxychloride,
$SOCl_2$=thionyl chloride,
TFA=trifluoroacetic acid,
TFMSA=trifluoromethanesulfonic acid
THF=tetrahydrofuran.

Methods of Using Compounds of the Disclosure

The compounds of the present disclosure are useful in the treatment of diseases characterized by disruption of or damage to cGMP/PKG and/or cAMP/PKA signaling mediated pathways, e.g., as a result of increased expression of PDE1 or decreased expression of cGMP/PKG or cAMP/PKA activity due to inhibition or reduced levels of inducers of cyclic nucleotide synthesis, such as dopamine and nitric oxide (NO). It is believed that by inhibiting PDE1, for example, that this action could reverse or prevent the attenuation of cGMP/PKG or cAMP/PKA signaling (e.g., enhance cGMP or cAMP, respectively). Therefore, administration or use of a preferred PDE1 inhibitor as described herein, e.g., a PDE1 inhibitor as hereinbefore described could provide a potential means to provide a treatment for various cardiovascular diseases and disorders.

In various embodiments, the present disclosure provides for a method [Method 1] of enhancing the effect of an adenosine $A_2$ receptor agonist in the treatment, mitigation or prophylaxis of a disease or condition characterized by inotropic and/or lusitropic dysfunction comprising administration of an effective amount of PDE1 inhibitor to a patient in need thereof. For example, the present disclosure provides for the following embodiments of Method 1:

1.1 Method 1, wherein the PDE1 inhibitor is one of Formula I', II', III' or IV' as hereinbefore described, in free or pharmaceutically acceptable salt form.

1.2 Method 1 or 1.1 wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one:

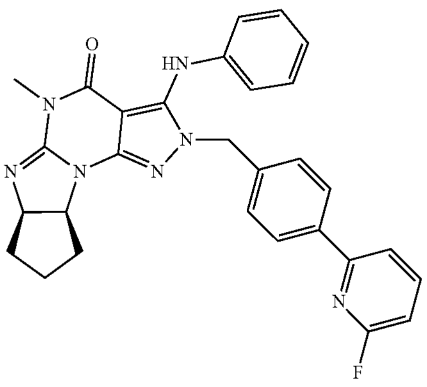 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

1.3 Method 1 or 1.1 wherein the PDE1 inhibitor is 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one:

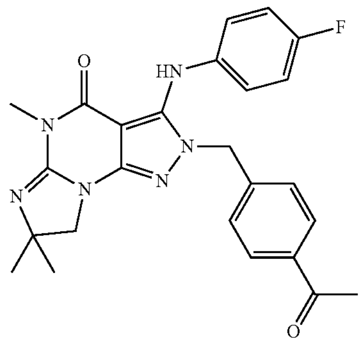 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

1.4 Method 1 or 1.1 wherein the PDE1 inhibitor is 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

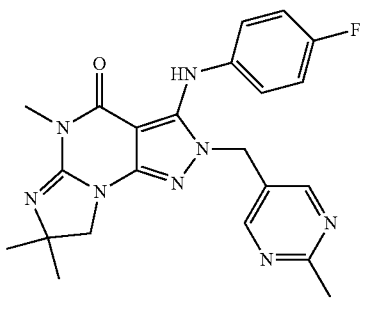 [SMILES: Cc1ncc(Cn2nc3c(c2Nc2ccc(F)cc2)C(=O)N(C)C2=NC(C)(C)CN23)cn1]

in free or pharmaceutically acceptable salt form.

1.5 Any of the preceding methods, wherein the disease or condition is angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, an inflammatory disease or disorder, fibrosis, cardiac hypertrophy, vascular remodeling, a connective tissue disease or disorder (e.g., Marfan Syndrome), chronic heart failure, myocardial ischemia, myocardial hypoxia, reperfusion injury, left ventricular dysfunctions (e.g., myocardial infarction, ventricular expansion), vascular leakage (i.e., consequent to hypoxia)) muscular dystrophy (e.g., Duchenne muscular dystrophy), or amyotrophic lateral sclerosis.

1.6 Any of the preceding methods, wherein the disease or condition to be treated is chronic heart failure, myocardial inflammation, fibrosis, myocardial ischemia, myocardial hypoxia, reperfusion injury, left ventricular dysfunctions (e.g., myocardial infarction, ventricular expansion), vascular leakage (i.e., consequent to hypoxia), acute vascular inflammation (i.e., consequent to vascular injury), or cardiac hypertrophy.

1.7 Method 1.6, wherein the disease or condition to be treated is chronic heart failure.

1.8 Method 1.6, wherein the disease or condition to be treated is myocardial inflammation.

1.9 Method 1.6, wherein the disease or condition to be treated is fibrosis.

1.10 Method 1.6, wherein the disease or condition to be treated is myocardial ischemia.

1.11 Method 1.6, wherein the disease or condition to be treated is myocardial hypoxia.

1.12 Method 1.6, wherein the disease or condition to be treated is reperfusion injury.

1.13 Method 1.6, wherein the disease or condition to be treated is a left ventricular dysfunction (e.g., myocardial infarction or ventricular expansion).

1.14 Method 1.6, wherein the disease or condition to be treated is vascular leakage (i.e., consequent to vascular injury).

1.15 Method 1.6, wherein the disease or condition to be treated is cardiac hypertrophy.

1.16 Any of the preceding methods, wherein the PDE1 inhibitor is administered to reduce the risk of injury to cardiac tissue due to ischemia or hypoxia.

1.17 Any of the preceding methods, wherein the PDE1 inhibitor is administered to reduce the risk of side effects due to adenosine $A_1$ receptor stimulation.

1.18 Any of the preceding methods, wherein the PDE1 inhibitor is administered to reduce the effective dose of an adenosine $A_2$ receptor agonist.

1.19 Any of the preceding methods, wherein the PDE1 inhibitor is administered in conjunction with another therapeutic agent selected from an adenosine $A_2$ agonist, a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl(peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; anti-anginal agents or combinations thereof.

1.20 Any of the preceding methods, wherein the PDE1 inhibitor is administered in conjunction with an additional therapeutic agent selected from an adenosine $A_2$ agonist, a beta-adrenergic receptor antagonist (i.e., a beta-blocker); ACE inhibitor, a calcium channel blocker; angiotensin receptor blockers (ARBs); neprilysin inhibitors or combinations thereof.

1.21 Any of methods 1.19 or 1.20 wherein the PDE1 inhibitor is administered simultaneously with the additional therapeutic agent.

1.22 Any of methods 1.19-1.21, wherein the PDE1 inhibitor is administered within 24 hours of the additional therapeutic agent; optionally within 12 hours of the additional therapeutic agent; optionally within 6 hours of the additional therapeutic agent; optionally within 3 hours of the additional therapeutic agent; optionally within 2 hours of the additional therapeutic agent; optionally within 1 hours of the additional therapeutic agent; optionally within 30 minutes of the additional therapeutic agent; optionally within 15 minutes of the additional therapeutic agent; optionally within 10 minutes of the additional therapeutic agent; optionally within 5 minutes of the additional therapeutic agent; or optionally within 1 minute of the additional therapeutic agent.

1.23 Any of the preceding methods, wherein the adenosine $A_2$ receptor agonist is an adenosine $A_{2B}$ receptor agonist.

1.24 Any of the preceding methods, wherein the adenosine $A_2$ receptor agonist comprises endogenous adenosine; e.g. any of the preceding methods, wherein the only adenosine $A_2$ receptor agonist enhanced by the PDE1 inhibitor is endogenous adenosine.

1.25 Any of the preceding methods, wherein the adenosine $A_2$ receptor agonist comprises a selective adenosine $A_{2B}$ receptor agonist.

1.26 Any of the preceding methods wherein enhancing the effect of an adenosine $A_2$ receptor agonist corresponds to enhancing or prolonging an adenosine $A_2$-mediated elevation of a cyclic nucleotide by inhibiting degradation of cAMP by PDE1.

1.27 Any of the preceding methods, wherein the PDE1 inhibitor is administered at a concentration of 0.01 mg/kg to 10 mg/kg.

1.28 Any of the preceding methods wherein the patient is a mammal which expresses PDE1C as the predominant PDE1 in cardiac tissue, e.g., a dog or a human.

1.29 Any of the preceding methods wherein the patient is a human.

1.30 Any of the preceding methods wherein the patient is a human and the PDE1 inhibitor is administered at an oral daily dosage of 1-10 mg.

1.31 Any of the preceding methods wherein the patient is a human, the PDE1 inhibitor is administered at an oral daily dosage of 0.5-20 mg, e.g., 1-10 mg, and the PDE1 inhibitor is selected from
   a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
   b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
   c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

1.32 Method 1.30 wherein the disease or condition characterized by inotropic and/or lusitropic dysfunction is heart failure.

The disclosure further provides a PDE1 inhibitor for use in a method of enhancing the effect of an adenosine $A_2$ receptor agonist in the treatment, mitigation or prophylaxis of a disease or condition characterized by inotropic and/or lusitropic dysfunction, e.g., for use in any of Methods 1, et seq.

The disclosure further provides the use of a PDE1 inhibitor in the manufacture of a medicament for enhancing the effect of an adenosine $A_2$ receptor agonist in the treatment, mitigation or prophylaxis of a disease or condition characterized by inotropic and/or lusitropic dysfunction, e.g., a medicament for use in any of Methods 1, et seq.

In various embodiments, the present disclosure provides for a method [Method 2] of enhancing adenosine $A_2$ receptor function in the treatment, mitigation or prophylaxis of a disease or condition characterized by impaired adenosine $A_2$ receptor function, comprising administration of an effective amount of a PDE1 inhibitor to a patient in need thereof. For example, the present disclosure provides for the following Methods:

2.1 Method 2, wherein the impaired adenosine $A_2$ receptor function is impaired adenosine $A_{2B}$ receptor function.

2.2 Any of the preceding methods, wherein the impaired adenosine $A_2$ receptor function is characterized by (i) impaired responsiveness of the adenosine $A_{2B}$ receptor to endogenous adenosine and/or (ii) impaired release and/or production of endogenous adenosine in response to cardiac damage or heart failure.

2.3 Any of the preceding methods, wherein the PDE1 inhibitor is one of Formula I', II', III', or IV', as hereinbefore described, in free or pharmaceutically acceptable salt form.

2.4 Any of the preceding methods wherein the PDE1 inhibitor is selected from
   a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
   b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
   c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

2.5 Any of the preceding methods, wherein the disease or condition to be treated is chronic heart failure, myocardial inflammation, fibrosis, myocardial ischemia, myocardial hypoxia, reperfusion injury, left ventricular dysfunctions (e.g., myocardial infarction, ventricular expansion), vascular leakage (i.e., consequent to hypoxia), acute vascular inflammation (i.e., consequent to vascular injury), or cardiac hypertrophy.

2.6 Method 2.2, wherein the disease or condition to be treated is chronic heart failure.

2.7 Method 2.2, wherein the disease or condition to be treated is myocardial inflammation.

2.8 Method 2.2, wherein the disease or condition to be treated is fibrosis.

2.9 Method 2.2, wherein the disease or condition to be treated is myocardial ischemia.

2.10 Method 2.2, wherein the disease or condition to be treated is myocardial hypoxia.

2.11 Method 2.2, wherein the disease or condition to be treated is reperfusion injury.

2.12 Method 2.2, wherein the disease or condition to be treated is a left ventricular dysfunction (e.g., myocardial infarction or ventricular expansion).

2.13 Method 2.2, wherein the disease or condition to be treated is vascular leakage (i.e., consequent to vascular injury).

2.14 Method 2.2, wherein the disease or condition to be treated is cardiac hypertrophy.

2.15 Any of the preceding methods, wherein the PDE1 inhibitor is administered to precondition or provide protection to cardiac tissue against ischemia or hypoxia.

2.16 Any of the preceding methods, wherein the PDE1 inhibitor is administered with an adenosine $A_2$ receptor agonist.

2.17 Method 2.13, wherein the PDE1 inhibitor is administered simultaneously with the adenosine $A_2$ receptor agonist.

2.18 Method 2.13, wherein the PDE1 inhibitor is administered after the adenosine $A_2$ agonist.

2.19 Method 2.13, wherein the PDE1 inhibitor is administered before the adenosine $A_2$ agonist.

2.20 Any of methods 2.13-2.16, wherein the PDE1 inhibitor is administered within 24 hours of the adenosine $A_2$ agonist; optionally within 12 hours of the adenosine $A_2$ agonist; optionally within 6 hours of the adenosine $A_2$ agonist; optionally within 3 hours of the adenosine $A_2$ agonist; optionally within 2 hours of the adenosine $A_2$ agonist; optionally within 1 hours of the adenosine $A_2$ agonist; optionally within 30 minutes of the adenosine $A_2$ agonist; optionally within 15 minutes of the adenosine $A_2$ agonist; optionally within 10 minutes of the adenosine $A_2$ agonist; optionally within 5 minutes of the adenosine $A_2$ agonist; or optionally within 1 minute of the adenosine $A_2$ agonist.

2.21 Any of the preceding methods, wherein the disease or condition is characterized by adenosine $A_{2B}$ receptor malfunction or hypofunctioning.

2.22 Any of methods 2.13-2.18, wherein the adenosine $A_2$ agonist is a selective adenosine $A_{2B}$ agonist.

2.23 Any of methods 2.13-2.19, wherein the PDE1 inhibitor is also administered in conjunction with another therapeutic agent selected from a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl(peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; antianginal agents or combinations thereof.

2.24 Any of the preceding methods, wherein the PDE1 inhibitor is administered in conjunction with an additional therapeutic agent selected from a beta-adrenergic receptor antagonist (i.e., a beta-blocker); ACE inhibitor, a calcium channel blocker; angiotensin receptor blockers (ARBs); neprilysin inhibitors or combinations thereof.

2.25 Any of the preceding methods, wherein the PDE1 inhibitor is administered at a concentration of 0.01 mg/kg to 10 mg/kg.

2.26 Any of the preceding methods, wherein the PDE1 inhibitor is administered at a concentration of 0.01 mg/kg to 10 mg/kg.

2.27 Any of the preceding methods wherein the patient is a mammal which expresses PDE1C as the predominant PDE1 in cardiac tissue, e.g., a dog or a human.

2.28 Any of the preceding methods wherein the patient is a human.

2.29 Any of the preceding methods wherein the patient is a human and the PDE1 inhibitor is administered at an oral daily dosage of 1-10 mg.

2.30 Any of the preceding methods wherein the patient is a human, the PDE1 inhibitor is administered at an oral daily dosage of 0.5-20 mg, e.g., 1-10 mg, and the PDE1 inhibitor is selected from a. (6aR,9aS)-5,6a,7,8,9,9a-hexahydro-5-methyl-3-(phenylamino)-2-((4-(6-fluoropyridin-2-yl)phenyl) methyl)-cyclopent[4,5]imidazo[1,2-a]pyrazolo[4,3-e]pyrimidin-4(2H)-one, in free or pharmaceutically acceptable salt form, e.g., monophosphate salt form;

b. 7,8-dihydro-2-(4-acetylbenzyl)-3-(4-fluorophenylamino)-5,7,7-trimethyl-[2H]-imidazo-[1,2-a] pyrazolo[4,3-e]pyrimidin-4(5H)-one, in free or pharmaceutically acceptable salt form; and c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

2.31 Method 2.30 wherein the disease or condition characterized by impaired adenosine $A_2$ receptor function is heart failure.

The disclosure further provides a PDE1 inhibitor for use in a method of enhancing adenosine $A_2$ receptor function in the treatment, mitigation or prophylaxis of a disease or condition characterized by impaired adenosine $A_2$ receptor function, e.g., for use in any of Methods 2, et seq.

The disclosure further provides the use of a PDE1 inhibitor in the manufacture of a medicament for enhancing adenosine $A_2$ receptor function in the treatment, mitigation or prophylaxis of a disease or condition characterized by impaired adenosine $A_2$ receptor function, e.g., a medicament for use in any of Methods 2, et seq.

Thus, in further embodiments, the present disclosure provides for a method [Method 3] of treating, mitigating or preventing cardiotoxicity consequent to administration of a chemotherapeutic agent and/or radiation therapy, comprising administration of an effective amount of a PDE1 inhibitor to a patient in need thereof. For example, the present disclosure provides for the following Methods:

3.1 Method 3, wherein the PDE1 inhibitor is administered in an amount effective to enhance adenosine $A_2$ signaling, e.g., in cardiomyocytes.

3.2 Method 3 or 3.1 wherein the cardiotoxicity is consequent to administration of a chemotherapeutic agent.

3.3 Method 3.3 wherein the chemotherapeutic agent is selected from anthracyclines, HER2 receptor blockers (e.g., trastuzumab), antimetabolites, alkylating agents, tyrosine kinase inhibitors (TKIs), angiogenesis inhibitors, and checkpoint inhibitors 3.4 Method 3.2 or 3.3, wherein the chemotherapeutic agent is an anthracycline.

3.5 Method 3.5 wherein the anthracycline is selected from daunorubicin, doxorubicin, epirubicin, idarubicin, sabarubicin, pixantrone, and valrubicin, 3.6 Method 3.4 wherein the anthracycline compound is doxorubicin.

3.7 Method 3.2 wherein the chemotherapeutic agent is selected from cyclophosphamide, ifosfamide, cisplatin, carmustine, busulfan, chlormethine, mitomycin, paclitaxel, etoposide, teniposide, the *vinca* alkaloids, fluorouracil, cytarabine, amsacrine, cladribine, asparaginase, tretinoin and pentostatin.

3.8 Method 3.2 wherein the chemotherapeutic agent is an antagonist of human epidermal growth factor receptor 2 (HER2)/neu.

3.9 Method 3.7 wherein the chemotherapeutic agent is a monoclonal antibody specific for human epidermal growth factor receptor 2 (HER2)/neu, e.g. trastuzumab.

3.10 Any preceding method wherein the cardiotoxicity is consequent to administration of radiation therapy (optionally in combination with administration of a chemotherapeutic agent).

3.11 Any preceding method, wherein the patient is suffering from a cancer or a tumor.

3.12 Any preceding method, wherein the patient is suffering from a tumor selected from one or more of acoustic neuroma, astrocytoma, chordoma, CNS lymphoma, craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhadomyoma, papilloma, seborrheic keratosis, skin adnexal tumors, hepatic adenomas, renal tubular adenoma, bile duct adenoma, transitional cell papilloma, hydatidiform moles, ganglioneuroma, meningoma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid,), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant schwannoma, malignant pheochromocytoma, malignant paraganglioma, melanoma, mercell cell neoplasm, cystosarcoma phylloides, or Wilms tumor.

3.13 Any preceding method, wherein the patient is suffering from a glioma, osteosarcoma, melanoma, leukemia, or neuroblastoma.

3.14 Any preceding method, wherein the patient is suffering from a glioma (e.g., ependymoma, astrocytoma, oligodendrogliomas, brain stem glioma, optic nerve glioma, or mixed gliomas, e.g., oligoastrocytomas).

3.15 Any preceding method, wherein the patient is suffering from an astrocytoma (e.g., glioblastoma multiform).

3.16 Any preceding method, wherein the patient is suffering from glioblastoma multiform.

3.17 Any preceding method, wherein the patient is suffering from a cancer.

3.18 Any preceding method, wherein the patient is suffering from leukemia.

3.19 Any preceding method, wherein the patient is suffering from a lymphoma, a lymphocytic leukemia or a myelogenous leukemia.

3.20 Any preceding method, wherein the method is for treating and/or mitigating cardiotoxicity.

3.21 Any preceding method wherein the patient is suffering from or has been diagnosed with overt heart failure secondary to cardiotoxicity of cancer therapy.

3.22 Any preceding method wherein the patient has been diagnosed with overt heart failure secondary to cardiotoxicity of cancer therapy using cardiovascular imaging, e.g., employing radionuclide imaging, echocardiography and/or magnetic resonance imaging.

3.23 Any preceding method wherein the patient is suffering from a cardiac condition consequent to chemotherapy and/or radiation therapy selected from left ventricular (LV) dysfunction, congestive heart failure (CHF), coronary vasospasm, angina, myocardial infarction, arrhythmias, systemic hypertension, pericardial effusion, pulmonary fibrosis and pulmonary hypertension 3.24 Any preceding method wherein the patient was suffering from a pre-existing cardiovascular disease prior to receiving chemotherapy and/or radiation therapy, e.g., selected from left ventricular (LV) dysfunction, congestive heart failure (CHF), coronary vasospasm, angina, myocardial infarction, arrhythmias, systemic hypertension, pericardial effusion, pulmonary fibrosis and pulmonary hypertension.

3.25 Any preceding method wherein the patient also treated with an additional cardioprotective agent, e.g., selected from iron chelators (e.g., dexrazoxane), angiotensin receptor blockers (ARBs), beta-blockers (e.g., carvedilol, metoprolol or nebivolol), angiotensin converting enzyme inhibitors (ACEI), statins, an antioxidant (i.e., dihydromyricetin, antioxidants from virgin olive oil, sesame oil, sesamin, salidroside, melatonin, glutathione, coenzyme Q10, vitamins, quercetin, isorhamnetin, cannabidiol, resveratrol), Mdivi-1, metformin, N-acetylcysteine, phenethylamines, amifostine, prostacyclin (PGI2), meloxicam, diazoxide, ferric carboxymaltose, lecithinizedhuman recombinant super oxide dismutase, ghrelin, L-carnitine, molsidomine, didox, α-Linolenic acid and nicorandil.

3.26 Any preceding method wherein the patient also treated with an additional cardioprotective agent, e.g., selected from angiotensin converting enzyme (ACE) inhibitors, angiotensin receptor blockers (ARBs), beta-blockers (e.g., carvedilol or nebivolol), and iron chelators (e.g., dexrazoxane).

3.27 Any preceding method wherein the cardiotoxicity is consequent to administration of a chemotherapeutic agent which inhibits adenosine $A_2$ signaling and/or adenosine $A_2$ receptor expression.

3.28 Any preceding method wherein the PDE1 inhibitor is administered at an oral daily dosage of 0.5-100 mg, e.g., 1-10 mg 3.29 Any preceding method wherein the PDE1 inhibitor is selected from
   a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
   b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
   c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

The disclosure further provides a PDE1 inhibitor for use in a method of treating, mitigating or preventing cardiotoxicity, e.g., for use in any of Methods 3, et seq.

The disclosure further provides the use of a PDE1 inhibitor in the manufacture of a medicament for of treating, mitigating or preventing cardiotoxicity, e.g., a medicament for use in any of Methods 3, et seq.

In still further embodiments, the present disclosure provides for a method [Method 4] of treating heart failure, comprising administering a pharmaceutically effective amount of a PDE1 inhibitor to a patient in need thereof, wherein administration of the PDE1 inhibitor is sufficient to induce inotropic, lusitropic and/or vasodilatory effect. For example, the present disclosure provides for the following Methods:

4.1 Method 4, wherein the PDE1 inhibitor is a compound according to one or more of Formula I', Ia, II', III', IV', V or VI as hereinbefore described, in free or pharmaceutically acceptable salt form.

4.2 Any of the preceding methods, wherein the PDE1 inhibitor is a compound according to Formula Ia.

4.3 Any of the preceding methods, wherein the PDE1 inhibitor is Any preceding method wherein the PDE1 inhibitor is selected from one or more of the following:
   a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
   b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
   c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

4.4 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free or pharmaceutically acceptable salt form.

4.5 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in a pharmaceutically acceptable salt form.

4.6 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in phosphate salt form.

4.7 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in monophosphate salt form.

4.8 Any of the preceding methods, wherein the PDE1 inhibitor is administered in an amount of about 0.5 mg to about 300 mg, wherein the amount is calculated as the free base equivalent.

4.9 Any of the preceding methods, wherein the PDE1 inhibitor is administered in an amount of about 1 mg to about 100 mg, wherein the amount is calculated as the free base equivalent.

4.10 Any of the preceding methods, wherein the PDE1 inhibitor is administered in an amount of about 10 mg to about 90 mg, wherein the amount is calculated as the free base equivalent.

4.11 Any of the preceding methods, wherein the PDE1 inhibitor is administered in an amount of about 30 mg to about 90 mg, wherein the amount is calculated as the free base equivalent.

4.12 Any of the preceding methods, wherein the PDE1 inhibitor is administered in an amount of about 10 mg, about 30 mg, or about 90 mg, wherein the amount is calculated as the free base equivalent.

4.13 Any of the preceding methods, wherein the PDE1 inhibitor is administered in an amount of about 30 mg, wherein the amount is calculated as the free base equivalent.

4.14 Any of the preceding methods, wherein the PDE1 inhibitor is administered to the patient one to ten times daily.

4.15 Any the preceding methods, wherein the PDE1 inhibitor is administered to the patient once daily.

4.16 Any of the preceding methods, wherein the PDE1 inhibitor is administered orally, sublingually or parenterally.

4.17 Any of the preceding methods, wherein the PDE1 inhibitor is administered orally.

4.18 Any of the preceding methods, wherein the PDE1 inhibitor is administered in an amount effective to induce an inotropic effect in the patient.

4.19 Any of the preceding methods, wherein the PDE1 inhibitor is administered in an amount effective to induce a lusitropic effect in the patient.

4.20 Any of the preceding methods, wherein the PDE1 inhibitor is administered in an amount effective to induce a vasodilatory effect in the patient.

4.21 Any of the preceding methods, wherein the PDE1 inhibitor is administered in an amount effective to induce both an inotropic effect and a vasodilatory in the patient.

4.22 Any of the preceding methods, wherein the PDE1 inhibitor is administered in an amount effective to induce an inotropic effect, a lusitropic effect and a vasodilatory effect in the patient.

4.23 Any of the preceding methods, wherein the patient is suffering from chronic systolic heart failure.

4.24 Any of the preceding methods, wherein the patient is suffering from acute decompensated HF.

4.25 Any of the preceding methods, wherein the patient is suffering from NYHA Class II heart failure or NYHA Class III heart failure.

4.26 Any of the preceding methods, wherein the patient is suffering from heart failure characterized by a low LVEF.

4.27 Any of the preceding methods, wherein the patient is suffering from heart failure characterized by a LVEF between 54% and 10%, or between 39% and 10%, or between 35% and 10%, or between 40% and 54%, or between 35% and 39%, or less than 35%.

4.28 Any of the preceding methods, wherein the patient is suffering from heart failure characterized by a LVEF of 35% or less.

4.29 Any of the preceding methods, wherein the patient is suffering from heart failure characterized by a LVEF between 10% and 35%.

4.30 Any of the preceding methods, wherein the PDE1 inhibitor is also administered in conjunction with another therapeutic agent selected from a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl (peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; antianginal agents or combinations thereof.

4.31 Any of the preceding methods, wherein the PDE1 inhibitor is administered in conjunction with an additional therapeutic agent selected from a beta-adrenergic receptor antagonist (i.e., a beta-blocker); ACE inhibitor, a calcium channel blocker; angiotensin receptor blockers (ARBs); neprilysin inhibitors or combinations thereof.

4.32 Any of the preceding methods, wherein the PDE1 inhibitor is administered in conjunction with an additional therapeutic agent selected from an angiotensin receptor blocker (ARB); a neprilysin inhibitor or a combination thereof 4.33 Any of the preceding methods, wherein the PDE1 inhibitor is administered in conjunction with an angiotensin receptor blocker and a neprilysin inhibitor.

4.34 Any of the preceding methods, wherein the PDE1 inhibitor is administered in conjunction with:

a. an angiotensin receptor blocker selected from angiocandesartan, eprosartan, irbesartan, losartan and valsartan or salts thereof, and b. a neprilysin inhibitor selected from phosphoramidon, thiorphan, candoxatrilat, candoxatril, sacubitril, or the compound of the Chemical Abstract Service (CAS) Number 115406-23-0 or salts thereof.

4.35 Any of the preceding methods, wherein the PDE1 inhibitor is administered in conjunction with valsartan and sacubitril.

The disclosure further provides a PDE1 inhibitor for use in a method of treating heart failure, e.g., for use in any of Methods 4, et seq.

The disclosure further provides the use of a PDE1 inhibitor in the manufacture of a medicament for use in a method of treating heart failure, e.g., a medicament for use in any of Methods 4, et seq.

In still further embodiments, the present disclosure provides for a method [Method 5] of inducing an inotropic, lusitropic and/or vasodilatory effect in a patient suffering from heart failure, comprising administering a pharmaceutically effective amount of a PDE1 inhibitor to a patient in need thereof. For example, the present disclosure provides for the following Methods:

5.1 Method 5, wherein the PDE1 inhibitor is a compound according to one or more of Formula I', Ia, II', III', IV', V or VI as hereinbefore described, in free or pharmaceutically acceptable salt form.

5.2 Any of the preceding methods, wherein the PDE1 inhibitor is a compound according to Formula Ia.

5.3 Any of the preceding methods, wherein the PDE1 inhibitor is Any preceding method wherein the PDE1 inhibitor is selected from one or more of the following:

d. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;

e. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and f. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

5.4 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in free or pharmaceutically acceptable salt form.

5.5 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in a pharmaceutically acceptable salt form.

5.6 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in phosphate salt form.

5.7 Any of the preceding methods, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one in monophosphate salt form.

5.8 Any of the preceding methods, wherein the PDE1 inhibitor is administered in an amount of about 0.5 mg to about 300 mg, wherein the amount is calculated as the free base equivalent.

5.9 Any of the preceding methods, wherein the PDE1 inhibitor is administered in an amount of about 1 mg to about 100 mg, wherein the amount is calculated as the free base equivalent.

5.10 Any of the preceding methods, wherein the PDE1 inhibitor is administered in an amount of about 10 mg to about 90 mg, wherein the amount is calculated as the free base equivalent.

5.11 Any of the preceding methods, wherein the PDE1 inhibitor is administered in an amount of about 30 mg to about 90 mg, wherein the amount is calculated as the free base equivalent.

5.12 Any of the preceding methods, wherein the PDE1 inhibitor is administered in an amount of about 10 mg, about 30 mg, or about 90 mg, wherein the amount is calculated as the free base equivalent.

5.13 Any of the preceding methods, wherein the PDE1 inhibitor is administered in an amount of about 30 mg, wherein the amount is calculated as the free base equivalent.

5.14 Any of the preceding methods, wherein the PDE1 inhibitor is administered to the patient one to ten times daily.

5.15 Any the preceding methods, wherein the PDE1 inhibitor is administered to the patient once daily.

5.16 Any of the preceding methods, wherein the PDE1 inhibitor is administered orally, sublingually or parenterally.

5.17 Any of the preceding methods, wherein the PDE1 inhibitor is administered orally.

5.18 Any of the preceding methods, wherein the PDE1 inhibitor is administered in an amount effective to induce an inotropic effect in the patient.

5.19 Any of the preceding methods, wherein the PDE1 inhibitor is administered in an amount effective to induce a lusitropic effect in the patient.

5.20 Any of the preceding methods, wherein the PDE1 inhibitor is administered in an amount effective to induce a vasodilatory effect in the patient.

5.21 Any of the preceding methods, wherein the PDE1 inhibitor is administered in an amount effective to induce both an inotropic effect and a vasodilatory effect in the patient.

5.22 Any of the preceding methods, wherein the PDE1 inhibitor is administered in an amount effective to induce an inotropic effect, a lusitropic effect and a vasodilatory effect in the patient.

5.23 Any of the preceding methods, wherein the patient is suffering from stable chronic systolic heart failure.

5.24 Any of the preceding methods, wherein the patient is suffering from acute decompensated HF.

5.25 Any of the preceding methods, wherein the patient is suffering from NYHA Class II heart failure or NYHA Class III heart failure.

5.26 Any of the preceding methods, wherein the patient is suffering from heart failure characterized by a low LVEF.

5.27 Any of the preceding methods, wherein the patient is suffering from heart failure characterized by a LVEF between 54% and 10%, or between 39% and 10%, or between 35% and 10%, or between 40% and 54%, or between 35% and 39%, or less than 35%.

5.28 Any of the preceding methods, wherein the patient is suffering from heart failure characterized by a LVEF of 35% or less.

5.29 Any of the preceding methods, wherein the patient is suffering from heart failure characterized by a LVEF between 10% and 35%.

5.30 Any of the preceding methods, wherein the PDE1 inhibitor is also administered in conjunction with another therapeutic agent selected from a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl (peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; anti-anginal agents or combinations thereof.

5.31 Any of the preceding methods, wherein the PDE1 inhibitor is administered in conjunction with an additional therapeutic agent selected from a beta-adrenergic receptor antagonist (i.e., a beta-blocker); ACE inhibitor, a calcium channel blocker; angiotensin receptor blockers (ARBs); neprilysin inhibitors or combinations thereof.

5.32 Any of the preceding methods, wherein the PDE1 inhibitor is administered in conjunction with an additional therapeutic agent selected from an angiotensin receptor blocker (ARB); a neprilysin inhibitor or a combination thereof 5.33 Any of the preceding methods, wherein the PDE1 inhibitor is administered in conjunction with an angiotensin receptor blocker and a neprilysin inhibitor.

5.34 Any of the preceding methods, wherein the PDE1 inhibitor is administered in conjunction with:

a. an angiotensin receptor blocker selected from angiocandesartan, eprosartan, irbesartan, losartan and valsartan or salts thereof, and b. a neprilysin inhibitor selected from phosphoramidon, thiorphan, candoxatrilat, candoxatril, sacubitril, or the compound of the Chemical Abstract Service (CAS) Number 115406-23-0 or salts thereof.

5.35 Any of the preceding methods, wherein the PDE1 inhibitor is administered in conjunction with valsartan and sacubitril.

Combination Therapies with PDE1 Inhibitors

In some embodiments, the PDE1 inhibitor is administered in combination with other therapeutic modalities. Thus, in addition to the therapies described above, one may also provide to the patient more pharmaceutical cardiac therapies. Examples of other therapies include, without limitation, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin receptor type 2 antagonists and cytokine blockers/inhibitors, and HDAC inhibitors. A particular form of combination therapy will include the use of PDE1 inhibitors.

Combinations may be achieved by administering a single composition or pharmacological formulation that includes the PDE1 inhibitor and one or more additional therapeutic agents, or by administration of two distinct compositions or formulations, separately, simultaneously or sequentially, wherein one composition includes the PDE1 inhibitor and the other includes the additional therapeutic agent or agents. The therapy using a PDE1 inhibitor may precede or follow administration of the other agent(s) by intervals ranging from minutes to weeks. In embodiments where the other agent and expression construct are applied separately to the cell, one would generally ensure that a significant period of time did not expire between the times of each delivery, such that the agent and expression construct would still be able to exert an advantageously combined effect on the cell. In some embodiments, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a PDE1 inhibitor, or an additional therapeutic agent will be desired. In this regard, various combinations may be employed. By way of illustration, where the PDE1 inhibitor is "A" and the additional therapeutic agent is "B," the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Non-limiting examples of a pharmacological therapeutic agent that may be used in the present invention include an adenosine $A_2$ agonist; a beta-adrenergic receptor antagonist (i.e., a beta-blocker); an ACE inhibitor; an angiotensin receptor blocker (ARBs); antihyperlipoproteinemic agent; an antiarteriosclerotic agent; an antithrombotic/fibrinolytic agent; a blood coagulant; an antiarrhythmic agent; an antihypertensive agent; a vasopressor; a treatment agent for congestive heart failure; an antianginal agent; an antibacterial agent; neprilysin inhibitors or a combination thereof. Other combinations are likewise contemplated. Some specific agents are described below.

Adenosine $A_2$ agonist: In various embodiments, the adenosine $A_2$ agonist used in the present combinations and methods may be either an adenosine $A_{2A}$ or adenosine $A_{2B}$ agonist. $A_{2A}$ receptor agonists include, but are not limited to, adenosine, CGS21680, ATL-146e, YT-146 (i.e., 2-(1-octynyl)adenosine), CGS-21680, DPMA (i.e., N-6-(2-(3,5-dimethoxyphenyl)-2-(2-methylphenyl)ethyl)adenosine), Regadenoson, UK-432,097, limonene, N-ethylcarboxyamidoadenosine, CV-3146, binodenoson and BVT.115959. $A_{2B}$ receptor agonists include, but are not limited to, (S)-PIPNECA, BAY 60-6583, LUF-5835, LUF-5845, and N-ethylcarboxyamidoadenosine.

Beta blockers: Various beta-adrenergic receptor antagonists, also called beta-blockers, are currently in clinical use for eliminating the harmful chronic myocardial stimulation which is caused by failing heart. Preferred beta-adrenergic receptor antagonists include metoprolol, metoprolol succinate, carvedilol, atenolol, propranolol, acebutolol, acebutolol HCL, betaxolol, betaxolol HCL, nadolol, talinolol, bisoprolol, bisoprolol hemifumarate, carteolol, carteolol HCL, esmolol, esmolol HCL, labetalol, labetalol HCL, metoprolol, metoprolol succinate, metoprolol tartrate, nadolol, penbutolol, penbutolol sulfate, pindolol, propranolol, propranolol HCL, sotalol, sotalol HCL, timolol and timolol hydrogen maleate salt or a pharmaceutically acceptable salt thereof. According to the invention, a beta-adrenergic receptor antagonist may be administered in daily doses, which are clinically accepted for such agents. For example, a suitable daily dose of metoprolol as a tartrate or succinate salt, is about 100-200 mg and for carvedilol about 5-50 mg depending upon the condition to be treated, the route of administration, age, weight and the condition of the patient.

Antihyperlipoproteinemics: In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof a. Aryloxyalkanoic Acid/Fibric Acid Derivatives: Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.
b. Resins/Bile Acid Sequesterants: Non-limiting examples of resins/bile acid sequesterants include cholestyramine (cholybar, questran), colestipol (colestid) and polidexide.
c. HMG CoA Reductase Inhibitors: Non-limiting examples of HMG CoA reductase inhibitors include lovastatin (mevacor), pravastatin (pravochol), simvastatin (zocor), atorvastatin (Lipitor) or rosuvastatin (crestor).
d. Nicotinic Acid Derivatives: Non-limiting examples of nicotinic acid derivatives include nicotinate, acepimox, niceritrol, nicoclonate, nicomol and oxiniacic acid.
e. Thyroid Hormones and Analogs: Non-limiting examples of thyroid hormones and analogs thereof include etoroxate, thyropropic acid and thyroxine.
f. Miscellaneous Antihyperlipoproteinemics: Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

Antiarteriosclerotics: Non-limiting examples of an antiarteriosclerotic include pyridinol carbamate.

Antithrombotic/Fibrinolytic Agents: In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants: A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents: Non-limiting examples of antiplatelet agents include aspirin, a dextran, dipyridamole (persantine), heparin, sulfinpyranone (anturane), ticlopidine (ticlid), clopidigrel (Plavix) and ticagrelor (Brilinta).

c. Thrombolytic Agents: Non-limiting examples of thrombolytic agents include tissue plasminogen activator (activase), plasmin, pro-urokinase, urokinase (abbokinase) streptokinase (streptase), anistreplase/APSAC (eminase).

Blood Coagulants: In certain embodiments wherein a patient is suffering from a hemorrhage or an increased likelihood of hemorrhaging, an agent that may enhance blood coagulation may be used. Non-limiting examples of a blood coagulation promoting agent include thrombolytic agent antagonists and anticoagulant antagonists.

a. Anticoagulant Antagonists: Non-limiting examples of anticoagulant antagonists include protamine and vitamin K.

b. Thrombolytic Agent Antagonists and Antithrombotics: Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Antiarrhythmic Agents: Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents.

a. Sodium Channel Blockers: Non-limiting examples of sodium channel blockers include Class IA, Class IB and Class IC antiarrhythmic agents. Non-limiting examples of Class IA antiarrhythmic agents include disopyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

b. Repolarization Prolonging Agents: Non-limiting examples of an agent that prolong repolarization, also known as a Class III antiarrhythmic agent, include amiodarone (cordarone) and sotalol (betapace).

c. Calcium Channel Blockers/Antagonist: Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

d. Miscellaneous Antiarrhythmic Agents: Non-limiting examples of miscellaneous antiarrhythmic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipratropium bromide, lidocaine, lorajmine, lorcainide, meobentine, moricizine, pirmenol, prajmaline, propafenone, pyrinoline, quinidine polygalacturonate, quinidine sulfate and viquidil.

Antihypertensive Agents: Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers: Non-limiting examples of an alpha blocker, also known as an α-adrenergic blocker or an α-adrenergic antagonist, include, amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers: In certain embodiments, an antihypertensive agent is both an alpha and beta adrenergic antagonist. Non-limiting examples of an alpha/beta blocker comprise labetalol (normodyne, trandate).

c. Anti-Angiotension II Agents: Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril, Ramipril, benazepril, moexipril, trandolapril and pharmaceutically acceptable salts thereof. Examples of salts of the ACE inhibitors include acid addition salts with organic or inorganic acids. Suitable organic carboxylic acids include salicylic acid, maleic acid, tartaric acid, citric acid, adipic acid, sorbic acid, malonic acid, 1,4-butanedioic acid, malic acid, pivalic acid, succinic acid, nicotinic acid, isonicotinic acid, furan-2-carboxylic acid, acetic acid, benzoic acid, fatty acids such as, for example, lauric acid, myristic acid or oleic acid, and suitable inorganic acids include, for example, hydrochloric acid, hydrobromic acid, hydriodic acid, nitric acid, sulfuric acid and/or phosphoric acid. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan or salts thereof d. Sympatholytics: Non-limiting examples of a sympatholytic include a centrally acting sympatholytic or a peripherally acting sympatholytic. Non-limiting examples of a centrally acting sympatholytic, also known as central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or an alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators: In certain embodiments a cardiovascular therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, trolnitrate phosphate and visnadine. In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives: Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil. In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quaternary ammonium compound, a reserpine derivative or a sulfonamide derivative.

Arylethanolamine Derivatives: Non-limiting examples of arylethanolamine derivatives include amosulalol, bufuralol, dilevalol, labetalol, pronethalol, sotalol and sulfinalol.

Benzothiadiazine Derivatives: Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethizide, methyclothiazide, meticrane, metolazone, paraflutizide, polythizide, tetrachlormethiazide and trichlormethiazide.

N-Carboxyalkyl(Peptide/Lactam) Derivatives: Non-limiting examples of N-carboxyalkyl(peptide/lactam) derivatives include alacepril, captopril, cilazapril, delapril, enalapril, enalaprilat, fosinopril, lisinopril, moveltopril, perindopril, quinapril and ramipril.

Dihydropyridine Derivatives: Non-limiting examples of dihydropyridine derivatives include amlodipine, felodipine, isradipine, nicardipine, nifedipine, nilvadipine, nisoldipine and nitrendipine.

Guanidine Derivatives: Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines: Non-limiting examples of hydrazines/phthalazines include budralazine, cadralazine, dihydralazine, endralazine, hydracarbazine, hydralazine, pheniprazine, pildralazine and todralazine.

Imidazole Derivatives: Non-limiting examples of imidazole derivatives include clonidine, lofexidine, phentolamine, tiamenidine and tolonidine.

Quaternary Ammonium Compounds: Non-limiting examples of quaternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives: Non-limiting examples of reserpine derivatives include bietaserpine, deserpidine, rescinnamine, reserpine and syrosingopine.

Sulfonamide Derivatives: Non-limiting examples of sulfonamide derivatives include ambuside, clopamide, furosemide, indapamide, quinethazone, tripamide and xipamide.

Vasopressors: Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Treatment Agents for Congestive Heart Failure: Non-limiting examples of agents for the treatment of congestive heart failure include anti-angiotension II agents, afterload-preload reduction treatment, diuretics and inotropic agents.

a. Afterload-Preload Reduction: In certain embodiments, an animal patient that cannot tolerate an angiotension antagonist may be treated with a combination therapy. Such therapy may combine administration of hydralazine (apresoline) and isosorbide dinitrate (isordil, sorbitrate).

b. Diuretics: Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

c. Inotropic Agents: Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, *digitalis*, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strophanthin, sulmazole, theobromine and xamoterol. In particular aspects, an inotropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents: Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

Guanylate cyclase stimulators: Non-limiting examples of guanylate cyclase stimulators includes riociguat.

Neprilysin (NEP) inhibitors: In one embodiment, the NEP inhibitors for use in the current invention are selective NEP inhibitors. In a further embodiment, the NEP inhibitors for use in the current invention are inhibitors with at least 300-fold selectivity for NEP inhibition over ACE inhibition. In a further embodiment, the NEP inhibitors for use in the current invention are inhibitors with at least 100-fold selectivity for NEP inhibition over ECE (Endothelin Converting Enzyme) inhibition. In yet another embodiment, the NEP inhibitors for use in the current invention are inhibitors with at least 300-fold selectivity for NEP inhibition over ACE inhibition and 100-fold selectivity for NEP inhibition over ECE inhibition.

In another embodiment, the NEP inhibitors for use in the current invention are the NEP inhibitors disclosed in the following patents, patent applications or non-patent publications: EP-1097719 B1, EP-509442A, U.S. Pat. No. 4,929,641, EP-599444B, US-798684, J. Med. Chem. (1993) 3821, EP-136883, U.S. Pat. No. 4,722,810, Curr. Pharm. Design (1996) 443, J. Med. Chem. (1993) 87, EP-830863, EP-733642, WO 9614293, WO 9415908, WO 9309101, WO 9109840, EP-519738, EP-690070, Bioorg. Med. Chem. Lett. (1996) 65, EP-A-0274234, Biochem. Biophys. Res. Comm. (1989) 58, Perspect. Med. Chem. (1993) 45, or EP-358398-B. The contents of these patents and publications are hereby incorporated by reference in their entirety herein. In another embodiment, the NEP inhibitors for use in the current invention are the NEP inhibitors Phosphoramidon, Thiorphan, Candoxatrilat, Candoxatril, or the compound of the Chemical Abstract Service (CAS) Number 115406-23-0.

In another embodiment, the NEP inhibitors for use in the current invention are the NEP inhibitors disclosed in US 2006/0041014 A1, the contents of which are hereby incorporated by reference in their entirety herein. In another embodiment, the NEP inhibitors for use in the current invention are the NEP inhibitors disclosed in U.S. Pat. No. 5,217,996, the contents of which are hereby incorporated by reference in their entirety herein. In another embodiment, the NEP inhibitors for use in the current invention are the NEP inhibitors disclosed in U.S. Pat. No. 8,513,244, the contents of which are hereby incorporated by reference in their entirety herein. In another embodiment, the NEP inhibitors for use in the current invention are the NEP inhibitors disclosed in U.S. Pat. No. 5,217,996, the contents of which are hereby incorporated by reference in their entirety herein. In another embodiment, the NEP inhibitors for use in the current invention are the NEP inhibitors disclosed in US patent application publication 2013/0330365, the contents of which are hereby incorporated by reference in their entirety herein. In another embodiment, the NEP inhibitors for use in the current invention are the NEP inhibitors disclosed in US patent application publication 2016/0038494, the contents of which are hereby incorporated by reference in their entirety herein.

Accordingly, in various embodiments, the present disclosure also provides for a pharmaceutical combination [Combination 1] for enhancing the effect of an adenosine $A_2$ receptor agonist in the treatment, mitigation or prophylaxis of a disease or condition characterized by inotropic and/or lusitropic dysfunction, e.g., in accordance with any of Method 1, et seq. or enhancing adenosine $A_2$ receptor function in the treatment, mitigation or prophylaxis of a disease or condition characterized by impaired adenosine $A_2$ receptor function, e.g. in accordance with any of Method 2, et seq., the pharmaceutical combination comprising an effective amount of a PDE1 inhibitor and one or more additional therapeutic agents.

1.1 Combination 1 wherein the PDE1 inhibitor and the one or more additional therapeutic agents are in a single dosage form, e.g., a tablet or capsule, in combination or association with a pharmaceutically acceptable diluent or carrier.

1.2 Combination 1 wherein the PDE1 inhibitor and the one or more additional therapeutic agents are in a single package, e.g., with instructions for administration simultaneously or sequentially.

1.3 Any of the preceding combinations, wherein the PDE1 inhibitor is one of Formula I', II', III', or IV', in free or pharmaceutically acceptable salt form, 1.4 Any of the preceding combinations wherein the PDE1 inhibitor is selected from a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;

b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

1.5 Any of the preceding combinations, wherein the one or more additional therapeutic agents are selected from an adenosine $A_2$ agonist, a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl(peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; antianginal agents or combinations thereof.

1.6 Any of the preceding combinations, wherein the additional therapeutic agent is selected from an adenosine $A_2$ agonist, a beta-adrenergic receptor antagonist (i.e., a beta-blocker); ACE inhibitor, a calcium channel blocker; angiotensin receptor blockers (ARBs); neprilysin inhibitors or combinations thereof.

1.7 Any of the preceding combinations, wherein the additional therapeutic agent is selected from an adenosine $A_2$ agonist.

1.8 Any of the preceding combinations, wherein the additional therapeutic agent is an adenosine $A_2$ agonist selected from CGS21680, ATL-146e, YT-146 (i.e., 2-(1-octynyl)adenosine), CGS-21680, DPMA (i.e., N-6-(2-(3,5-dimethoxyphenyl)-2-(2-methylphenyl)ethyl)adenosine), Regadenozone, UK-432,097, limonene, N-ethylcarboxyamidoadenosine, CV-3146, binodenoson and BVT.115959, (S)-PHPNECA, BAY 60-6583, LUF-5835, or LUF-5845.

1.9 Any of the preceding combinations, wherein the additional therapeutic agent is a selective $A_{2B}$ agonist.

1.10 Any of the preceding combinations, wherein the additional therapeutic agent is a selective $A_{2B}$ agonist selected from (S)-PHIPNECA, BAY 60-6583, LUF-5835, LUF-5845, and N-ethylcarboxyamidoadenosine.

1.11 Any of the preceding combinations, wherein the disease or condition to be treated is angina, stroke, renal failure, essential hypertension, pulmonary hypertension, secondary hypertension, isolated systolic hypertension, hypertension associated with diabetes, hypertension associated with atherosclerosis, renovascular hypertension, congestive heart failure, an inflammatory disease or disorder, fibrosis, cardiac hypertrophy, vascular remodeling, a connective tissue disease or disorder (e.g., Marfan Syndrome), chronic heart failure, myocardial ischemia, myocardial hypoxia, reperfusion injury, left ventricular dysfunctions (e.g., myocardial infarction, ventricular expansion), vascular leakage (i.e., consequent to hypoxia)), muscular dystrophy (e.g., Duchenne muscular dystrophy), or amyotrophic lateral sclerosis.

1.12 Any of the preceding combinations, wherein the PDE1 inhibitor is administered to precondition or provide protection to cardiac tissue against ischemia or hypoxia.

1.13 Any of the preceding combinations, further comprising one or more of a beta-adrenergic receptor antagonist (i.e., a beta-blocker); ACE inhibitor; Neprilysin inhibitors; antihyperlipoproteinemics (e.g., an aryloxyalkanoic/fibric acid derivative, a resin/bile acid sequesterant, a HMG CoA reductase inhibitor, a nicotinic acid derivative, a thyroid hormone or thyroid hormone analog or a combination thereof); antiarteriosclerotics (e.g., pyridinol carbamate); guanylate cyclase activators; antithrombotic and/or fibrinolytic agents (e.g., anticoagulants, anticoagulant antagonists, antiplatelet agents, thrombolytic agents, thrombolytic agent antagonists); blood coagulants (e.g., thrombolytic agent antagonists and anticoagulant antagonists); anti-arrhythmic agents (e.g., sodium channel blockers, repolarization prolonging drugs, calcium channel blockers); anti-hypertensive agents (e.g., sympatholytic, alpha/beta blockers, alpha blockers, anti-angiotensin II agents, beta blockers, calcium channel blockers, vasodilators); arylethanolamine derivatives; benzothiadiazine derivatives; N-carboxyalkyl(peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; or antianginal agents.

In some embodiments, the present disclosure also provides for a pharmaceutical combination [Combination 2] for treating, mitigating or preventing cardiotoxicity, e.g., in accordance with any of Method 3, et seq., the pharmaceutical combination comprising an effective amount of a PDE1 inhibitor and one or more additional cardioprotective agents.

2.1 Combination 2 wherein the PDE1 inhibitor and the one or more additional therapeutic agents are in a single dosage form, e.g., a tablet or capsule, in combination or association with a pharmaceutically acceptable diluent or carrier.

2.2 Combination 2 wherein the PDE1 inhibitor and the one or more additional therapeutic agents are in a single package, e.g., with instructions for administration simultaneously or sequentially.

2.3 Any of the preceding combinations, wherein the PDE1 inhibitor is one of Formula I', II', III' or IV', in free or pharmaceutically acceptable salt form.

2.4 Any of the preceding combinations wherein the PDE1 inhibitor is selected from e. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;

f. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and g. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

2.5 Any of the preceding combinations, wherein the one or more additional cardioprotective agents is selected from iron chelators (e.g., dexrazoxane), angiotensin receptor blockers (ARBs), beta-blockers (e.g., carvedilol, metoprolol or nebivolol), angiotensin converting enzyme inhibitors (ACEI), statins, an antioxidant (i.e., dihydromyricetin, antioxidants from virgin olive oil, sesame oil, sesamin, salidroside, melatonin, glutathione, coenzyme Q10, vitamins, quercetin, isorhamnetin, cannabidiol, resveratrol), Mdivi-1, metformin, N-acetylcysteine, phenethylamines, amifostine, prostacyclin (PGI2), meloxicam, diazoxide, ferric carboxymaltose, lecithinizedhuman recombinant super oxide dismutase, ghrelin, L-carnitine, molsidomine, didox, α-Linolenic acid and nicorandil.

2.6 Any of the preceding combinations, wherein the one or more additional cardioprotective agents is selected from angiotensin converting enzyme (ACE) inhibitors, angiotensin receptor blockers (ARBs), beta-blockers (e.g., carvedilol or nebivolol), and iron chelators (e.g., dexrazoxane).

"PDE1 inhibitor" as used herein describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

The phrase "Compounds of the Disclosure" or "PDE 1 inhibitors of the Disclosure", or like terms, encompasses any and all of the compounds disclosed herewith, e.g., a Compound of Formula I, Formula II, Formula III, Formula IV, Formula V, Formula VI, Formula VII, Formula VIII, Formula IX, Formula X, or Formula XI.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "precondition" as used herein is intended to refer to treatment of cardiac tissue to produce resistance to the loss of blood supply or to oxygen. Ischemic preconditioning is an intrinsic process whereby repeated short episodes of ischemia protect the myocardium against a subsequent ischemic insult.

The term "patient" include human or non-human (i.e., animal) patient. In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, unrecited elements or method steps.

The term "heart failure" as used herein refers to a condition in which the heart is unable to pump sufficiently to maintain blood flow to meet the body's needs. The term heart failure may be synonymous with the terms congestive heart failure (CHF) and congestive cardiac failure (CCF). Signs and symptoms of heart failure commonly include shortness of breath, excessive tiredness, and leg swelling. Heart failure may be assessed via left ventricle ejection fraction (LVEF), which is a measurement of blood quantity pumped out of the left ventricle of the heart with each contraction. A LVEF of 35% or less is considered severely below normal and marks moderate to severe heart failure.

The term NYHA Class II heart failure refers to the second class of heart failure as designated by the New York Heart Association (NYHA) Classification System. Class II heart failure is characterized by a slight limitation of physical activity. Ordinary physical activity results in fatigue, palpitation, dyspnea, or anginal pain. Patients with NYHA Class II heart failure are comfortable at rest.

The term NYHA Class III heart failure refers to the third class of heart failure as designated by the New York Heart Association (NYHA) Classification System. Class III heart failure is characterized by marked limitation of physical activity. Less than ordinary activity causes fatigue, palpitation, dyspnea, or anginal pain. Patients with NYHA Class III heart failure are comfortable at rest. As used herein, masses relating to drug load and/or dosage refer to the mass of the relevant compound's free base equivalent. Thus, even when a PDE1 inhibitor compound as described herein is provided in salt form, its mass is calculated and referred to as the free base equivalent, unless otherwise indicated. For example, a dose of 30 mg of (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, calculated as the free base equivalent, would correspond to about 36 mg of the monophosphate salt of Compound 1.

Compounds of the Disclosure, e.g., Formula I, II, III, IV, V, VI, VII, VIII, IX, X, and XI as hereinbefore described, in free or pharmaceutically acceptable salt form, may be used as a sole therapeutic agent, but may also be used in combination or for co-administration with other active agents.

Dosages employed in practicing the present disclosure will of course vary depending, e.g. on the particular disease or condition to be treated, the particular Compound of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Disclosure, together with a pharmaceutically acceptable diluent or carrier therefor.

Pharmaceutical compositions comprising Compounds of the Disclosure may be prepared using conventional diluents or excipients and techniques known in the galenic art. Thus, oral dosage forms may include tablets, capsules, solutions, suspensions and the like.

EXAMPLES

Example 1: PDE1A Vs PDE1C Isoform Expression in Canine/Rabbit Versus Mouse/Rat In order to establish an experimental model in a mammal expressing primarily PDE1C in the myocardium, protein and gene expression are examined in human, dog, rabbit, rat, and mouse. Heart tissue is rapidly excised from euthanized adult C57BL/6J mice, Sprague Dawley rats, mongrel dogs, and New Zealand White Rabbits, washed and then frozen in liquid nitrogen. Human myocardial tissue is obtained from donor control hearts and end-stage cardiomyopathic hearts (explanted), from a tissue bank at the University of Pennsylvania. Hearts were harvested under controlled surgical procedures using ice-cold cardioplegia, transported on ice and snap-frozen in liquid nitrogen shortly thereafter. Tissue is then analyzed for PDE1A, 1, and 1C mRNA expression and protein expression, using species-specific primers and antibodies.

RNA is extracted from frozen tissue by acid guanidinium thiocyanate-phenol-chloroform method using TRIzol Reagent (Thermo Fisher Scientific Inc., Waltham, MA). 1 μg of RNA is reverse transcribed to cDNA using a High Capacity cDNA Reverse Transcription Kit (Thermo Fisher Scientific) and T100 thermal cycler (Bio-Rad Laboratories, Inc., Hercules, California). Real-time PCR is performed with TaqMan Gene Expression Master Mix or Power SYBR Green PCR Master Mix (Thermo Fisher Scientific) using a CFX384 Real-Time System (Bio-Rad Laboratories). TaqMan primers/probes (Thermo Fisher Scientific) are used for PCR analysis of human, dog, rat and mouse tissue. Relative mRNA expression level is determined by the ΔΔCt method. Primer sequences for rabbit are as follows: PDE1A (F) 5'-TGGTGGCCCAGTCACAAATA-3' (R) 5'-AATGGTGGTTGAACTGCTTG-3'; PDE1B (F) 5'-CTGTCGGAGATCGAGGTCTTG-3' (R) 5'-GGTGCCCGTGTGCTCATAG-3'; PDE1C (F) 5'-CAGATGGAATAAAGCGGCATTC-3' (R) 5'-GGCAAGGTGAGACGACTTGTAGA-3'; GAPDH (F) 5'-TGGTGAAGGTCGGAGTGAAC-3' (R) 5'-ATGTAGTGGAGGTCAATGAATGG-3'.

Frozen tissue is homogenized and sonicated in RIPA lysis buffer. After centrifugation (XX, 30 min) protein concentration is determined by BCA Assay (Thermo Fisher Scientific) from the supernatant. Equal amounts of protein are loaded onto tris-glycine gels and run at 100 V for 75-90 min. Gel protein is transferred to nitrocellulose membranes by semi-dry blotting using the Trans-Blot Turbo Transfer System (Bio-Rad). Membranes are incubated with primary antibodies at 4° C. overnight. Following incubation with fluorescence-labeled secondary antibodies (LI-COR, Inc., Lincoln, NE) and a wash, the signal is detected using the Odyssey Imaging System (LI-COR). Antibodies are as follows: PDE1A (sc-50480, Santa Cruz Biotechnology; ab96336, Abcam), PDE1B (ab182565, Abcam), PDE1C (sc-376474, Santa Cruz Biotechnology; ab14602, Abcam), GAPDH (#2118, Cell Signaling Technology; ab9484, Abcam; IMG-3073, Imgenex).

It is thus found that human, dog and rabbit myocardium express primarily PDE1C, with a smaller amount of PDE1A, which is opposite of the profile in rat or mouse myocardium. The expression profile is not significantly altered by heart failure in dogs. Human left ventricle (LV) overwhelmingly expresses PDE1C at the transcript level, though some PDE1A is also present. At the protein level, both are present, with PDE1C dominating in normals, and PDE1A increasing with end-stage heart failure. PDE1B is undetected in heart for any of the tested species, but present in the brain.

Example 2: In Vivo Analysis of PDE1 Inhibition on Large Mammals (i.e., Dogs) in Normal and Failing Hearts Studies are conducted to test the effect of a potent PDE1 inhibitor (Compound 1) in two PDE1C-expressing mammals, dogs and rabbits, in both normal and failing hearts, and the results were contrasted with beta-adrenergic modulation. These animals are chosen because they express PDE1C>>PDE1A at mRNA and protein levels in myocardial tissue.

Compound 1 (molecular weight=605, (6aR,9aS)-2-(4-(6-fluoropyridin-2-yl)benzyl)-5-methyl-3-(phenyl-amino)-5,6a,7,8,9,9a-hexahydrocyclopenta-[4,5]imidazo[1,2-a]pyrazolo[4,3-e]pyrimidin-4-(2H)-one monophosphate) [alternative name for (6aR,9aS)-5,6a,7,8,9,9a-hexahydro-5-methyl-3-(phenylamino)-2-((4-(6-fluoropyridin-2-yl) phenyl)methyl)-cyclopent[4,5]imidazo[1,2-a]pyrazolo[4,3-e]pyrimidin-4(2H)-one monophosphate, described supra], is synthesized by Intra-Cellular Therapies, Inc. (New York, NY). Its $K_i$s for full-length recombinant r-hPDE1A, 1, and 1C are 34, 380, and 37 μM, respectively, with >1000-fold greater activity toward PDE1 isoforms compared with the next nearest PDE family enzyme, PDE4D ($K_i$=33 nM) and $10^4$-$3\times10^5$-fold selectivity compared with all other PDE enzyme families. Additional pharmaceuticals used in the following examples are dobutamine (Hospira Inc., Lake Forest, IL), esmolol HCl (Mylan, Rockford, IL), MRS1754 (Tocris Bioscience, Bristol, UK), and Hespan (6% Hetastarch in 0.9% NaCl B. Braun Medical Inc., Bethlehem, PA).

In Vivo Canine Studies Method

Adult mongrel dogs (25-30 kg; n=6) are chronically instrumented with left ventricular sonomicrometers, micromanometers, inferior vena caval cuff occluders, and indwelling arterial and venous catheters for conscious pressure-volume hemodynamic analysis. Dogs are studied in the conscious state before and after inducing dilated cardiomyopathy by tachypacing for two weeks at 200 bpm. These dogs are studied on separate days to determine the effects of oral and intravenous Compound 1, and its interaction with β1-adrenergic stimulation.

Oral drug administration: Compound 1 (0.1-10 mg/kg) is administered in gelatin capsules in peanut butter, and hemodynamic data recorded over the ensuing hour. In a subset of animals, dogs are first subjected to dobutamine infusion for 15 minutes (10 μg/kg/min), a new baseline was established, and then oral dosages of Compound 1 are administered, with dobutamine subsequently added as a combination treatment 90 min after administration of Compound 1.

Intravenous drug administration: Compound 1 is dissolved in 0.05 M citrate-phosphate buffer, and administered as a bolus over the course of 1-2 minutes via a central venous catheter. The study employs two doses, 0.01 and 0.1 mg/kg, the latter administered 30 minutes after the first.

Intravenous blood is placed in K2EDTA tubes, centrifuged at 2,000 g for 15 min, plasma decanted, and stored frozen. Compound 1 levels are assessed by a rapid, sensitive liquid chromatography-tandem mass spectrometric (LC/MS-MS) method. A single liquid-liquid extraction step with acetonitrile containing 1% formic acid is employed for analysis of Compound 1, followed by a vacuum filtration to remove lipids using Waters Ostro Plates.

HPLC separation is performed on an Ascentis® Express Phenyl Hexyl column of dimensions 50 mm×3 mm, 2.7 μm with the internal standard of deuterated Compound 1. The mobile phase consists of a gradient of 60-100% methanol over 4.5 minutes in 5 mM ammonium bicarbonate with 0.2% NH3H2O, pumped at a flow rate of 0.8 mL/min. Analysis time is 4.5 min and both the analyte and internal standard eluted around 2.0 min. Multiple reactions monitoring (MRM) mode is used to detect Compound 1. MS is operated in the positive ion detection mode. The precursor to product ions (Q1→Q3) selected for Compound 1 and internal standard during quantitative optimization were (m/z) 508.1→321.1 and 513.1→325.1 respectively. Calibration curves are linear from 0.02-500 ng/mL in dog plasma sample matrices. The lower limit of quantification (LLOQ) for plasma was 0.02 ng/mL.

In an initial dose titration study, normal conscious dogs are exposed to doses of Compound 1 ranging from 0.1-10 mg/kg, PO, and pharmacodynamics assays were performed. At 10 mg P.O., 120 min post dose, plasma Compound 1 concentrations are 103.9±8.5 ng/mL in normal dogs and 178.4±100.5 ng/mL in HF dogs. At 0.1 mg/kg i.v. in normal dogs, plasma Compound 1 concentrations peaked within minutes, falling to 211.2±60.7 at 10 min, and 94.5±21.2 ng/mL at 30 min. In failing dogs, plasma Compound 1 levels after IV administration were 441.4±92.5 at 10 min, and 184.9±28.9 ng/mL at 30 min.

Acute PDE1 Inhibition Alters Cardiovascular Function in Normal and Failing Canine Hearts To assess the effect of acute PDE1 inhibition, studies were conducted of the pressure-volume relationships in intact dogs with either healthy or failing hearts, and analyzed hemodynamic and cardiac mechanics at baseline and two hours after oral administration of Compound 1 (10 mg/kg). In both control and heart failure (HF) dogs, there was an increase in contractility (higher end-systolic elastance) with little change in LV preload (end-diastolic volume) or systolic pressure. In normal dogs, Compound 1 increased heart rate, reduced systemic vascular resistance, and increased cardiac output, without altering systolic blood pressure. Load insensitive indexes of contractility ($dP/dt_{max}$/IP and PRSW) increased. Relaxation reflected by peak rate of pressure decline ($dP/dt_{min}$) and relaxation time constant (tau) also improved. Similar drug effects, in particular in contractility and vasodilation, were observed in HF dogs. Increased heart rates were blunted in HF animals (p=0.07 for interaction by 2-way ANOVA). Thus, the net effect of Compound 1 was to augment cardiac output by 50% in controls (32% in HF), without altering systemic pressure.

Intravenous Compound 1 produces similar effects in both normal and HF conditions, but the response was more rapid, peaking after 5-10 minutes. At 0.01 mg/kg (23.6±8.6 ng/mL plasma Compound 1 concentrations at 10 min), responses in all but heart rate were negligible at this dose. However, at 0.1 mg/kg (211.2±60.7 ng/mL plasma Compound 1 concentrations at 10 min), positive chronotropic, inotropic, lusitropic, and vasodilator responses were observed, with a net rise in cardiac output similar to that with 10 mg/kg oral dose. These effects were again slightly abated with heart failure, but inotropy, lusitropy, and vasodilation remained significantly improved.

Hemodynamic Effects of PDE1 Inhibition are Additive to Dobutamine

The acute cardiovascular effects of Compound 1 suggested a cAMP rather than cGMP-related response. This raised the question of whether its net impact was redundant to or amplified co-activation of the beta-adrenergic pathway with dobutamine. 10 μg/kg/min dobutamine was administered to dogs with or without 10 mg/kg Compound 1. Dobutamine increased PV loop area (indicating stroke work) and shifted the upper corner of each loop to the left (indicating increased contractility); adding Compound 1 further enhanced both. These effects were observed to be additive. This was quantified by assessing an interaction term from a 2-way ANOVA. Similar results were obtained in control and failing hearts.

Blood plasma is obtained from these animals, and cAMP and cGMP are assayed by ELISA. Dobutamine (but not Compound 1) augmented plasma cAMP in normal dogs, and the rise was similar with or without Compound 1. In HF dogs, cAMP is higher at baseline, and not significantly changed by the drugs (1-way RMANOVA, p=0.3), though their combination is significantly higher. Plasma cGMP remains unchanged at all conditions in normal and HF models.

Cardiovascular Effects of PDE1 Inhibition are Independent of Beta-Adrenergic Signaling, but Require Adenosine $A_{2B}$ Receptor Signaling.

Cyclic AMP is generated largely by transmembrane adenylyl cyclases activated via stimulatory G protein (Gs), with β-adrenergic, adenosine (primarily $A_{2M}$), glucagon, prostanoids, histamine, and serotonin all coupling to Gs in cardiomyocytes. The present studies focus on beta-adrenergic and adenosine receptors, and for the latter, concentrated on the $A_{2B}$ receptor, which has been reported to directly stimulate cAMP-dependent contractility. Anesthetized rabbits are administered a bolus intravenous Compound 1 at 0.1 mg/kg (dose based on dog results) with or without prior treatment with the selective β1-blocker esmolol or the adenosine $A_{2B}$R blocker MRS-1754. As in the dog, acute PDE1 inhibition alone increases cardiac output due to a rise in contractility (end-systolic elastance and pre-load recruitable stroke work rose by 50%), modestly elevated heart rate, and lowered systemic resistance, with no change in systolic pressure. Relaxation changes are also modest with LV preload (end-diastolic and volume) unaltered; however, the combined vasodilator-inotropic response doubled ventricular/arterial coupling ratio, Ees/Ea.

These experiments are then repeated after administering esmolol to block beta-AR receptors. While Compound 1 no longer increases HR, its contractile and vasodilation effects remain intact. Importantly, this esmolol dose effectively blocked cardiac responses to 10 μg/kg/min dobutamine. In a separate set of rabbits, Compound 1 is administered with or without the $A_{2B}$R blocker, MRS-1754. This eliminated all of the cardiovascular responses to Compound 1 including heart rate, contractility, and vasodilation. Neither inhibitor pretreatment alone has a significant impact on cardiovascular hemodynamics. Thus, $A_{2B}$R but not beta-AR signaling is required for the acute cardiovascular effects of PDE1 inhibition by Compound 1, except for heart rate which is also prevented by beta-AR blockade.

Heart rate itself influences cardiac function and hemodynamics, and as this differed between animals treated with Compound 1 alone or together with esmolol or MRS-1754, additional studies are performed in which rabbits were atrially paced at ~20% above the sinus node rate to fix heart rate constant. Compound 1 induces nearly identical responses under these conditions as when heart rate is allowed to change, and these effects are again unaltered by esmolol but fully blocked by MRS-1754.

Example 2: In Vivo Analysis of PDE1 Inhibition on Small Mammals (i.e., Rabbits) in Normal and Failing Hearts In Vivo Rabbit Studies Method New Zealand White rabbits (male, 2-3 kg) are sedated with 35 mg/kg ketamine and 5 mg/kg xylazine, intubated and ventilated (Model 683, Harvard Apparatus, Holliston, MA), with anesthesia maintained with isoflurane inhalation (1-2%). A pressure-volume catheter (SPR-894, Millar, Inc., Houston, TX) is inserted via the common carotid artery and advanced to the LV apex, and a 2-Fr pacing catheter is positioned in the right atrium via the right jugular vein to provide atrial pacing. A 4-Fr Berman balloon catheter (AI-07134, Teleflex, Wayne, PA) is positioned in the inferior vena cava (IVC) via a femoral vein to transiently obstruct venous return and to prevent variations in preloading. The parallel conductance is determined by the hypertonic saline injection method. Rabbits are infused with 6% hetastarch in saline during the procedure to stabilize arterial pressure. All pharmaceuticals are administered i.v.: A) Compound 1 (0.1 mg/kg) as a bolus injection over 1-2 minutes with or without pre-injection of the β1 receptor antagonist esmolol (0.5 mg/kg bolus injection followed by 0.05 mg/kg/min continuous infusion). These doses are also tested against 10 μg/kg/min dobutamine to demonstrate the efficacy of beta-adrenergic receptor blockade. B) Compound 1 (0.1 mg/kg) with or without bolus injection of the adenosine $A_{2B}$ receptor antagonist MRS1754 (1 mg/kg iv).

Intravenous blood is placed in K2EDTA tubes, centrifuged at 2,000 g for 15 min, plasma decanted, and stored frozen. Compound 1 levels are assessed by a rapid, sensitive liquid chromatography-tandem mass spectrometric (LC/MS-MS) method. A single liquid-liquid extraction step with acetonitrile containing 1% formic acid is employed for analysis of Compound 1, followed by a vacuum filtration to remove lipids using Waters Ostro Plates.

HPLC separation is performed on an Ascentis® Express Phenyl Hexyl column of dimensions 50 mm×3 mm, 2.7 μm with the internal standard of deuterated Compound 1. The mobile phase consists of a gradient of 60-100% methanol over 4.5 minutes in 5 mM ammonium bicarbonate with 0.2% NH3H2O, pumped at a flow rate of 0.8 mL/min. Analysis time is 4.5 min and both the analyte and internal standard eluted around 2.0 min. Multiple reactions monitoring (MRM) mode is used to detect Compound 1. MS is operated in the positive ion detection mode. The precursor to product ions (Q1→Q3) selected for Compound 1 and internal standard during quantitative optimization were (m/z) 508.1→321.1 and 513.1→325.1 respectively. Calibration curves are linear from 0.02-500 ng/mL in dog plasma sample matrices. The lower limit of quantification (LLOQ) for plasma was 0.02 ng/mL.

Rabbit dosing at 0.1 mg/kg i.v. yields plasma values of 213±88 ng/mL at 15 min. Mouse plasma levels 15 minutes after i.v. dosing was 334+/−74 ng/mL. Therapeutic levels are 100-300 ng/mL, and so analysis is presented after 120 min for P.O. and after 20 min for i.v. (somewhat sooner in rabbit and mouse due to faster kinetics).

Compound 1 Enhances cAMP-Mediated Contractility in Isolated Rabbit Cardiomyocytes To test whether PDE1 inhibition directly impacts cardiomyocyte contraction and calcium transients, studies are carried out on normal adult rabbit myocytes. As a control, isoproterenol (Iso, 50 nM) is administered, which increases both sarcomere shortening and peak $Ca^{2+}$ and accelerates the decay time of both. By contrast, Compound 1 has no effect even at 1 mM. The addition of a broad PDE inhibitor (IBMX, 100 μM) increased shortening and contraction/calcium decay rates, but did not alter peak calcium transients. As PDE1 requires sufficient cAMP and $Ca^{2+}$ to be impactful, a dose response was performed to the adenylate cyclase activator, forskolin (FSK) to determine the lowest dose producing a modest but significant inotropic effect (1 μM). When this dose is applied first, the addition of Compound 1 significantly increases shortening and relaxation/calcium decay rates. Peak calcium transient remains unaltered.

Time-controls tests are performed comparing Compound 1+FSK with FSK incubation for the identical duration. This confirms that the rise in sarcomere shortening with Compound 1 exceeds that with FSK alone. Comparing FSK alone, FSK+Compound 1, and FSK+IBMX, the relative rise in sarcomere shortening percentage with selective PDE1 inhibition is 31% of the rise with IBMX. For calcium relaxation, however, Compound 1 shortens the time constant by 67% of the maximal achieved with IBMX.

Example 3: In Vivo Analysis of PDE1 Inhibition on Mice in Normal and Failing Hearts Compound 1 has No Acute Cardiovascular Effects in Intact Mice The isoform disparity between dog, rabbit, and mice predicted that the mouse may not respond similarly to acute Compound 1 since PDE1A regulation of cAMP is much less relative to PDE1C. To test this, mice were administered the same or higher intravenous bolus doses (0.1, 0.5 mg/kg) as used in dogs and rabbits, and studied using a similar preparation to the rabbit. Results showed that even at a higher dose, the murine heart, which predominantly expresses PDE1A, failed to show any significant hemodynamic or cardiac changes.

Example 4: Comparisons of and Conclusions from Studies of PDE1 Inhibition in Normal and Failing Hearts The tests of Examples 1-3 reveal potent cardiovascular effects from a highly selective PDE1 inhibitor (Compound 1) that in our experimental models requires prominent expression of the PDE1C in the LV myocardium, a condition existing in humans. Negligible responses were observed in mice that express principally PDE1A. This is the first report of cardiovascular effects of PDE1 inhibition in larger mammals and we believe the results have translational relevance. Compound 1 is found to increase contractility and lusitropy (similar to 10 μg/kg/min dobutamine), with systemic vasodilation but minimal venodilation. The result is a net rise in cardiac output without altering arterial systolic pressure.

Unlike in vivo beta-AR stimulation, PDE1 inhibition does not raise plasma cAMP, and the effects are not suppressed by beta-AR blockade, but are prevented by $A_{2B}R$ inhibition. While these changes are associated with a faster heart rate, they are not driven by it, as rate change is blunted by heart failure and blocked by esmolol or fixed rate pacing, yet inotropic/vasodilator effects persist. Rabbit myocyte data shows PDE1 regulates AC-stimulated cAMP to modify contraction and rate of calcium transient decay, but not peak calcium; the latter also differing from beta-AR stimulation. Taken together, the profile of Compound 1 and its efficacy in a HF model indicates novel mechanisms with clinical potential.

While Compound 1 does not induce changes in plasma cyclic nucleotide in vivo, its augmentation of myocyte shortening, relaxation, and calcium decay kinetics only with priming AC stimulation supports targeting of cAMP. Both the lack of plasma rise in cAMP in vivo and peak myocyte calcium transient in vitro with Compound 1 further support that different cAMP compartments are being modulated between beta-AR stimulation and PDE1 inhibition. This is most directly supported by the failure of esmolol to block Compound 1 effects in the rabbit model. These results are important, since HF therapies that enhance cAMP, such as dobutamine and PDE3 inhibitors, have been historically useful acutely, but detrimental if used chronically. The profile of Compound 1, engaging an adenosine rather than beta-AR receptor pathway predicts different cardiovascular impacts despite sharing a cAMP signal.

The heart expresses multiple adenosine receptors, including $A_1$, $A_{2A}$, $A_{2B}$, and $A_3$. Both $A_1R$ and $A_3R$ couple to inhibitory G-proteins ($G_{i,0}$) and $G_{q/11}$ signaling, and blunt beta-AR stimulation. In contrast, both $A_{2A}$ and $A_{2B}$ couple with stimulatory $G_s$-cAMP, though regulation of contraction by the former may relate to blunting $A_1R$-anti-adrenergic effects, while $A_{2B}R$ reportedly has more direct effects. Previous studies have reported the importance of the $A_{2B}R$ in ischemic protection, and benefits in human heart failure. Thus far, studies have confirmed only that $A_{2B}R$ couples to PDE3B regulation in hepatocytes and PDE4D in pulmonary airway epithelial cells, so the present data linking it to PDE1 is novel.

PDE1 is found in the soluble fraction of myocytes and displays a striated distribution pattern that may reflect T-tubule mitochondria junctions. The lack of peak calcium rise in myocytes from Compound 1 (+FSK) supports a distribution of PDE1 away from the L-type calcium channel known by PDE3 and PDE4. $A_{2B}R$ is also found in vascular tissue and fibroblasts, where it regulates proliferation, vascular tone, and provide anti-fibrotic signaling. Intriguingly, PDE1 inhibition is also antifibrotic via a pathway involving both cAMP and cGMP (a caveat of this study was it was performed in rat and mouse), and plays an important role in smooth muscle proliferation. Thus, linkage of PDE1 inhibition with the $A_{2B}$ pathway may well have implications beyond acute hemodynamics.

Example 5: Effects of Compound 1 on Myocyte Contractility and Calcium in Comparison to PDE3 Inhibition in Isolated Rabbit Myocytes Rabbit myocytes were isolated to determine the effect of PDE1 inhibition on cardiomyocyte contraction and whole cell Ca2+ transients, and to compare the results to those with a PDE3 inhibitor, cilostamide (Cil, 1 μM). Percent sarcomere shortening and peak-Ca2+ transients rose and their decay kinetics accelerated in cells treated with Cil; however, this was not observed with Compound 1 (1 μM).

To compare the influence of PDE1 and PDE3 in modulating 3-AR signaling, cells were first exposed to a non-saturating dose of isoproterenol (Iso), then Iso combined with either Cil or Compound 1. As expected, Iso increased sarcomere shortening and peak-$Ca^{2+}$, and quickened relaxation times. Addition of Cil further increased sarcomere shortening (p=0.0002) and peak-$Ca^{2+}$ remained elevated over baseline (p=0.001). It was observed that when Compound 1 was added to Iso, sarcomere shortening did not change further, and peak-Ca2+ was no longer significantly different from pre-Iso baseline. This shows that PDE1 does not interact with 3-AR signaling, but PDE3 does.

An alternative approach to augmenting cAMP independent of 3-AR is to directly stimulate adenylate cyclase using forskolin (Fsk). A dose response study was carried out to identify a non-saturating Fsk dose that still generated significant inotropic effects (1 μM). Adding Cil to Fsk resulted in an increase in sarcomere shortening, peak-Ca2+ transient, and faster decay of the Ca2+ transient. When Compound 1 was added to FSK, sarcomere shortening rose as with Cil, but there was no corresponding increase in peak Ca2+ transient which was significantly less than with Cil. Surprisingly, the combination of FSK and Compound 1 enhanced the Ca2+ decay rate similarly to Cil.

Lastly, the effect of Iso, Cil, Compound 1, and their combination on myocyte cAMP was tested. Despite increases in sarcomere shortening and Ca2+ transients, Iso, Cil, and their combination did not measurably increase whole cell cAMP. Neither did Compound 1 or the combination of Iso and Compound 1. This is consistent with prior studies showing locally generated cAMP from β-AR and its modulation by PDE3 occur in local subcellular domains that are not easily detected in whole cell lysates32. Fsk resulted in a rise in cAMP, and though unaltered by addition of Cil, it substantially increased by adding Compound 1. The latter reached about half the maximal change as assessed by adding the broad PDE inhibitor IBMX to Fsk. Taken together, these data identify a different pool of cAMP under PDE1 regulation that is not modulated by β-AR but can be revealed with direct adenylate cyclase stimulation.

These studies reveal disparities between PDE1 and PDE3 inhibitory effects. PDE3 inhibition enhances contraction and peak-Ca2+ transients and amplifies β-AR stimulation, whereas PDE1 inhibition does not. PDE1 inhibition augments Fsk-stimulated cAMP and cell shortening without increasing Ca2+, whereas PDE3 inhibition increases both shortening and Ca2+, yet does not increase whole-cell measurable cAMP. Collectively, these results define a pharmacological profile of Compound 1 that is different from β-AR agonism and PDE3 inhibition, and suggests potential utility as a clinical HF therapeutic engaging novel mechanisms.

In the current study, evidence for microdomain regulation by PDE1 was provided by the whole cell cAMP measurements that showed little change despite Iso, Cil, or Iso+Cil stimulation, all of which (at the same concentrations) at doses we showed stimulated myocyte function and calcium handling. Fsk stimulates cAMP synthesis in multiple compartments as it targets adenylate cyclase directly, and here we detected a rise in cAMP that further increased with Compound 1; the combination of Iso and Compound 1 did not alter cAMP. This is consistent with a prior study employing FRET biosensors in adult mouse myocytes where a rise in cAMP with PDE1 inhibition was impacted by Fsk and not 3-AR co-stimulation. That cAMP appeared similar to Fsk and Fsk+Cil further supports different compartments being engaged.

While the sub-cellular cAMP signaling compartment(s) controlled by PDE1 were not specifically probed, the results provide substantial evidence supporting differences to cAMP regulation by R-AR activation or PDE3 inhibition. PDE1 failed to potentiate β-AR stimulation (in vivo and in vitro), unlike what occurs with PDE3 inhibition. In addition, Compound 1 did not augment whole-$Ca^{2+}$ transients whereas this is observed with Iso stimulation +/−PDE3 inhibition. The lack of $Ca^{2+}$ increase was still seen even when Compound 1 did enhance cell function, as when combined with Fsk. By contrast, PDE3 inhibition increased both function and $Ca^{2+}$. This is notable as prior safety concerns regarding PDE3 inhibitors often noted their effects on increasing myocyte $Ca^{2+}$, including arrhythmia. The lack of intracellular $Ca^{2+}$ increase despite functional improvement suggest PDE1 inhibition likely enhances phosphorylation of sarcomere proteins to improve myofilament calcium sensitivity. Furthermore, the ability of Compound 1 to accelerate the rate of $Ca^{2+}$ decline even as peak levels were slightly reduced, which suggests it also modulates internal $Ca^{2+}$ recycling and less so intracellular $Ca^{2+}$ entry.

Example 6: Cardiac and Hemodynamic Effects of Acute Phosphodiesterase-1 Inhibition in Human Heart Failure A Phase Ib/IIa, multi center, double-blind, randomized, placebo-controlled single ascending dose study of Compound 1 in patients with stable chronic systolic HF (NYHA Class II-II, LVEF≤35%) was conducted to evaluate the impact of a single oral dose of Compound 1 on cardiac systolic and diastolic function. Participants were randomized 3:1 in 3-groups of 12 to receive either Compound 1 at 10 mg, 30 mg, 90 mg. A further group was administered placebo. All patients were male or female ages 18 to 80 with NYHA class II-III heart failure, who were on stable drug failure heart medication and have exhibited an LVEF equal to or below 35% by echocardiogram obtained within the prior 6 months.

Hemodynamic monitoring began 30-60 minutes prior to the pre-dose echocardiogram through to 5-6 hours post-dose. Hemodynamic outcomes included LV volumes, LVEF, mean LV power index (mean power/$EDV^2$), effective arterial elastance (Ea=systolic BP*0.9/stroke volume), and estimated systemic vascular resistance (SVR=mean BP/CO) at 120 minutes post-dose (approximate Cmax in humans).

Administration of Compound 1 was shown to significantly decrease systemic vascular resistance across all cohorts, with 30 mg showing the greatest decrease. Effective arterial elastance also decreased in patients administered 30 mg and 90 mg of Compound 1. While all patients also showed an increase in mean power index (mPWRi) and cardiac output (CO), patients administered 30 mg compound 1 showed significantly greater increases in both mPRWi and CO in comparison with placebo. All dose amounts of Compound 1 were shown to decrease mean arterial blood pressure versus placebo.

Supine and orthostatic blood pressure and heart rate were recorded pre-dose, as well as 60 and 40 minutes post-dose. Continuous electrocardiographic monitoring starting up to 30-60 minutes prior to the pre-dose echocardiogram through to 5-6 hours post-dose including measurement of ectopic arrhythmias pre- and post-dose. Throughout the testing period, all patients' blood pressures and heart rates remained stable, and no patient developed sustained supraventricular or ventricular tachycardia. Additionally, none of the patients developed atrial fibrillation or atrial flutter, and there was no evidence of ventricular proarrhythmia in any of the patients.

Taken together, Compound 1, especially when administered at 30 mg, significantly increased cardiac power (mean power index) and cardiac output compared to placebo. SVR and Ea decreased at 30 and 90 mg doses. Cmax in plasma occurred at 90-120 minutes post-administration, with area under curve increasing with dose escalation. Compound 1 was found to be safe and well tolerated in patients with systolic heart failure (HFrEF).

What is claimed is:

1. A method of treating NYHA Class II chronic systolic heart failure or NYHA Class III chronic systolic heart failure, comprising administering a pharmaceutically effective amount of a PDE1 inhibitor to a patient in need thereof, wherein administration of the PDE1 inhibitor is sufficient to induce inotropic, lusitropic and/or vasodilatory effect, wherein the PDE1 inhibitor is one of:

A) a compound according to Formula I':

Formula I'

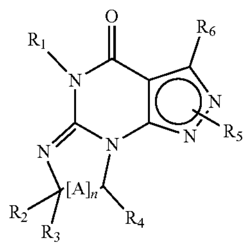

wherein (i) $R_1$ is H or $C_{1-4}$ alkyl;

(ii) $R_4$ is H or $C_{1-4}$ alkyl and $R_2$ and $R_3$ are, independently, H or $C_{1-4}$ alkyl, aryl, heteroaryl, (optionally hetero) arylalkoxy, or (optionally hetero) arylalkyl; or $R_2$ is H and $R_3$ and $R_4$ together form a di-, tri- or tetramethylene bridge;

(iii) $R_5$ is a substituted heteroarylalkyl; or $R_5$ is attached to one of the nitrogens on the pyrazolo portion of Formula I' and is a moiety of Formula A'

Formula A'

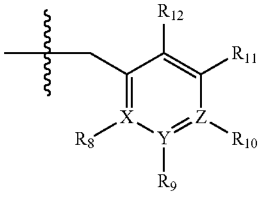

wherein X, Y and Z are, independently, N or C, and $R_8$, $R_9$, $R_{11}$ and $R_{12}$ are independently H or halogen, and $R_{10}$ is halogen, alkyl, cycloalkyl, haloalkyl, aryl, heteroaryl optionally substituted with halogen, thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl, arylamino, heteroarylamino, N,N-dialkylamino, N,N-diarylamino, or N-aryl-N-(arylalkyl) amino; and (v) n=0 or 1;

(vi) when n=1, A is —$C(R_{13}R_{14})$— wherein $R_{13}$ and $R_{14}$, are, independently, H or $C_{1-4}$ alkyl, aryl, heteroaryl, (optionally hetero) arylalkoxy or (optionally hetero) arylalkyl;

in free, salt or prodrug form, including its enantiomers, diastereoisomers and racemates;

B) a compound according to Formula Ia:

Formula Ia

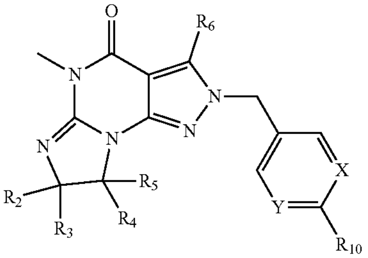

wherein (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;

(ii) $R_6$ is (optionally halo- or hydroxy-substituted) phenylamino, (optionally halo- or hydroxy-substituted) benzylamino, $C_{1-4}$alkyl, or $C_{1-4}$alkyl sulfide;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and X and Y are independently C or N, in free, pharmaceutically acceptable salt or prodrug form, including its enantiomers, diastereoisomers and racemates;

C) a compound according to Formula II':

Formula II'

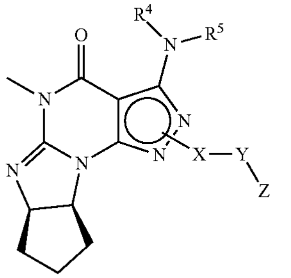

(i) X is $C_{1-6}$alkylene;

(ii) Y is a single bond, alkynylene, arylene or heteroarylene;

(iii) Z is H, aryl, heteroaryl, halo, halo$C_{1-6}$alkyl, —C(O)—$R^1$, —$N(R^2)(R^3)$, or $C_{3-7}$ cycloalkyl optionally containing at least one atom selected from a group consisting of N or O;

(iv) $R^1$ is $C_{1-6}$alkyl, halo$C_{1-6}$alkyl, —OH or —$OC_{1-6}$ alkyl;

(v) $R^2$ and $R^3$ are independently H or $C_{1-6}$alkyl;

(vi) $R^4$ and $R^5$ are independently H, $C_{1-6}$alkyl or aryl optionally substituted with one or more halo, hydroxy or $C_{1-6}$alkoxy;

(vii) wherein X, Y and Z are independently and optionally substituted with one or more halo, $C_{1-6}$alkyl, or halo$C_{1-6}$alkyl, in free or salt form;

D) a compound according to Formula III':

Formula III'

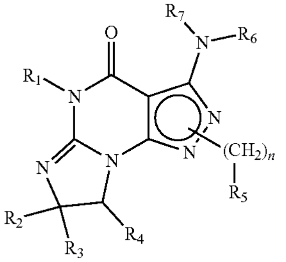

wherein (i) $R_1$ is H or $C_{1-4}$ alkyl;

(ii) $R_2$ and $R_3$ are independently H or $C_{1-6}$ alkyl;

(iii) $R_4$ is H or $C_{1-4}$ alkyl;

(iv) $R_5$ is aryl optionally substituted with one or more groups independently selected from —C(=O)—$C_{1-6}$ alkyl and $C_{1-6}$-hydroxyalkyl;

(v) $R_6$ and $R_7$ are independently H or aryl optionally substituted with one or more groups independently selected from $C_{1-6}$ alkyl and halogen; and (vi) n is 1, 2, 3, or 4, in free or salt form;

E) a compound according to Formula IV':

Formula IV'

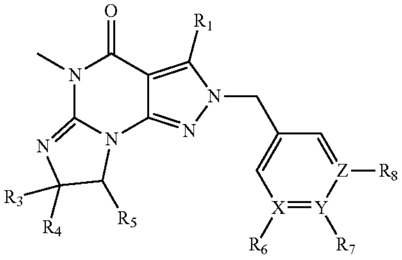

in free or salt form, wherein (i) $R_1$ is $C_{1-4}$alkyl, or —$NH(R_2)$, wherein $R_2$ is phenyl optionally substituted with halo;

(ii) X, Y and Z are, independently, N or C;

(iii) $R_3$, $R_4$ and $R_5$ are independently H or $C_{1-4}$alkyl; or $R_3$ is H and $R_4$ and $R_5$ together form a tri-methylene bridge, (iv) $R_6$, $R_7$ and $R_8$ are independently:

H, $C_{1-4}$alkyl, pyrid-2-yl substituted with hydroxy, or

—$S(O)_2$—$NH_2$;

provided that when X, Y and/or Z are N, then $R_6$, $R_7$ and/or $R_8$, respectively, are not present; and when X, Y and Z are all C, then at least one of $R_6$, $R_7$ or $R_8$ is —$S(O)_2$—$NH_2$ or pyrid-2-yl substituted with hydroxy;

F) a compound according to Formula V:

Formula V

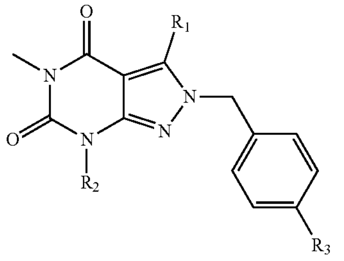

wherein (i) $R_1$is —NH ($R_4$), wherein $R_4$ is phenyl optionally substituted with halo;

(ii) $R_2$ is H or $C_{1-6}$alkyl;

(iii) $R_3$ is —$SO_2NH_2$ or —COOH;

in free or salt form; or

G) a compound according to Formula VI:

Formula VI

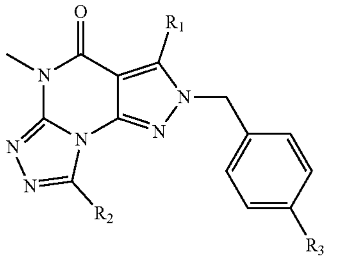

wherein (i) $R_1$ is —NH($R_4$), wherein $R_4$ is phenyl optionally substituted with halo;

(ii) $R_2$ is H or $C_{1-6}$alkyl;

(iii) $R_3$ is H, halogen, $C_{1-6}$alkyl, aryl optionally substituted with halogen, heteroaryl optionally substituted with halogen, or acyl, in free or salt form.

2. The method according to claim 1, wherein the PDE1 inhibitor is selected from a) (6aR,9aS)-5,6a, 7,8,9,9a-hexahydro-5-methyl-3-(phenylamino)-2-((4-(6-fluoropyridin-2-yl)phenyl) methyl)-cyclopent[4,5]imidazo [1,2-a]pyrazolo [4,3-e] pyrimidin-4 (2H)-one, in free or pharmaceutically acceptable salt form;

b) 7,8-dihydro-2-(4-acetylbenzyl)-3-(4-fluorophenylamino)-5,7,7-trimethyl-[2H]-imidazo-[1,2-a]pyrazolo [4,3-e]pyrimidin-4 (5H)-one, in free or pharmaceutically acceptable salt form; and c) 3-((4-fluorophenyl) amino)-5,7,7-trimethyl-2-((2-methylpyrimidin-5-yl)methyl)-7,8-dihydro-2H-imidazo [1,2-a]pyrazolo [4,3-e]pyrimidin-4 (5H)-one, in free or pharmaceutically acceptable salt form.

3. The method according to claim 1, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo [1,2-a]pyrazolo [4,3-e]pyrimidin-4 (2H)-one in phosphate salt form.

4. The method according to claim 1, wherein the PDE1 inhibitor is administered in an amount of about 10 mg to about 90 mg, wherein the amount is calculated as the free base equivalent.

5. The method according to claim 1, wherein the PDE1 inhibitor is administered in an amount of about 30 mg, wherein the amount is calculated as the free base equivalent.

6. The method according to claim 1, wherein the PDE1 inhibitor is administered to the patient once daily.

7. The method according to claim 1, wherein the PDE1 inhibitor is administered in an amount effective to induce both an inotropic effect and a vasodilatory in the patient.

8. The method according to claim 1, wherein the patient is suffering from NYHA Class II chronic systolic heart failure or NYHA Class III chronic systolic heart failure characterized by a low LVEF.

9. The method according to claim 1, wherein the patient is suffering from NYHA Class II chronic systolic heart failure or NYHA Class III chronic systolic heart failure characterized by a LVEF between 54% and 10%, or between 39% and 10%, or between 35% and 10%, or between 40% and 54%, or between 35% and 39%, or less than 35%.

10. The method according to claim 1, wherein the patient is suffering from NYHA Class II chronic systolic heart failure or NYHA Class III chronic systolic heart failure characterized by a LVEF of 35% or less.

11. The method according to claim 1, wherein the PDE1 inhibitor is administered in conjunction with another therapeutic agent selected from a beta-adrenergic receptor antagonist; ACE inhibitor; Neprilysin inhibitors; antihyperlipoproteinemics; antiarteriosclerotics; guanylate cyclase activators; antithrombotic and/or fibrinolytic agents; blood coagulants; anti-arrhythmic agents; anti-hypertensive agents; arylethanolamine derivatives; benzothiadiazine derivatives; N-carboxyalkyl (peptide/lactam) derivatives; dihydropyridine derivatives; guanidine derivatives; hydrazines/phthalazines; imidazole derivatives; quaternary ammonium compounds; reserpine derivatives; sulfonamide derivatives; vasopressors; diuretics; inotropic agents; anti-anginal agents or combinations thereof.

12. The method according to claim 1, wherein the PDE1 inhibitor is administered in conjunction with an additional therapeutic agent selected from an angiotensin receptor blocker (ARB); a neprilysin inhibitor or a combination thereof.

13. The method according to claim 1, wherein the PDE1 inhibitor is administered in conjunction with an angiotensin receptor blocker and a neprilysin inhibitor.

14. The method according to claim 1, wherein the PDE1 inhibitor is administered in conjunction with:

a) an angiotensin receptor blocker selected from angio-candesartan, eprosartan, irbesartan, losartan and valsartan or salts thereof; and b) a neprilysin inhibitor selected from phosphoramidon, thiorphan, candoxatrilat, candoxatril, sacubitril, or the compound of the Chemical Abstract Service (CAS) Number 115406-23-0 or salts thereof.

15. A method of inducing an inotropic, lusitropic and/or vasodilatory effect in a patient suffering from NYHA Class II chronic systolic heart failure or NYHA Class III chronic systolic heart failure, comprising administering a pharmaceutically effective amount of a PDE1 inhibitor to a patient in need thereof, wherein the PDE1 inhibitor is one of:

A) a compound according to Formula I':

Formula I'

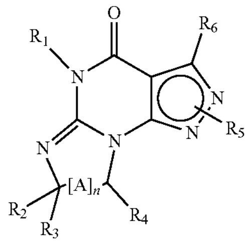

wherein (i) $R_1$ is H or $C_{1-4}$ alkyl;

(ii) $R_4$ is H or $C_{1-4}$ alkyl and $R_2$ and $R_3$ are, independently, H or $C_{1-4}$ alkyl, aryl, heteroaryl, (optionally hetero) arylalkoxy, or (optionally hetero) arylalkyl; or $R_2$ is H and $R_3$ and $R_4$ together form a di-, tri- or tetramethylene bridge;

(iii) $R_5$ is a substituted heteroarylalkyl;

or $R_5$ is attached to one of the nitrogens on the pyrazolo portion of Formula I' and is a moiety of Formula A'

Formula A'

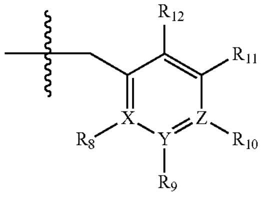

wherein X, Y and Z are, independently, N or C, and $R_8$, $R_9$, $R_{11}$ and $R_{12}$ are independently H or halogen, and $R_{10}$ is halogen, alkyl, cycloalkyl, haloalkyl, aryl, heteroaryl optionally substituted with halogen, thiadiazolyl, diazolyl, triazolyl, tetrazolyl, arylcarbonyl, alkylsulfonyl, heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl, arylamino, heteroarylamino, N,N-dialkylamino, N,N-diarylamino, or N-aryl-N-(arylalkyl) amino; and (v) n=0 or 1;

(vi) when n=1, A is —$C(R_{13}R_{14})$— wherein $R_{13}$ and $R_{14}$, are, independently, H or $C_{1-4}$ alkyl, aryl, heteroaryl, (optionally hetero) arylalkoxy or (optionally hetero) arylalkyl;

in free, salt or prodrug form, including its enantiomers, diastereoisomers and racemates;

B) a compound according to Formula Ia:

Formula Ia

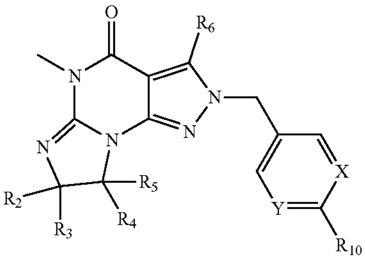

wherein (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;

(ii) $R_6$ is (optionally halo- or hydroxy-substituted) phenylamino, (optionally halo- or hydroxy-substituted) benzylamino, $C_{1-4}$alkyl, or $C_{1-4}$alkyl sulfide;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and X and Y are independently C or N, in free, pharmaceutically acceptable salt or prodrug form, including its enantiomers, diastereoisomers and racemates;

C) a compound according to Formula II':

Formula II'

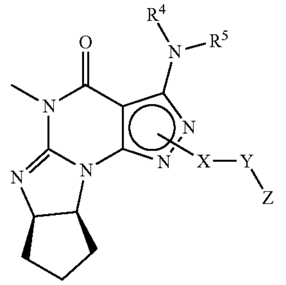

(i) X is $C_{1-6}$alkylene;

(ii) Y is a single bond, alkynylene, arylene or heteroarylene;

(iii) Z is H, aryl, heteroaryl, halo, halo$C_{1-6}$alkyl, —C(O)—$R^1$, —$N(R^2)$ $(R^3)$, or $C_{3-7}$ cycloalkyl optionally containing at least one atom selected from a group consisting of N or O;

(iv) $R^1$ is $C_{1-6}$alkyl, halo$C_{1-6}$alkyl, —OH or —$OC_{1-6}$ alkyl;

(v) $R^2$ and $R^3$ are independently H or $C_{1-6}$alkyl;

(vi) $R^4$ and $R^5$ are independently H, $C_{1-6}$alkyl or aryl optionally substituted with one or more halo, hydroxy or $C_{1-6}$alkoxy;

(vii) wherein X, Y and Z are independently and optionally substituted with one or more halo, $C_{1-6}$alkyl, or halo$C_{1-6}$ alkyl, in free or salt form;

D) a compound according to Formula III':

Formula III'

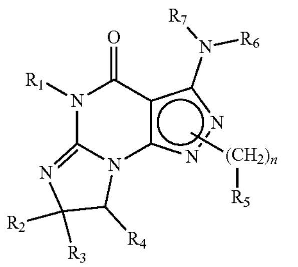

wherein (i) $R_1$ is H or $C_{1-4}$ alkyl;

(ii) $R_2$ and $R_3$ are independently H or $C_{1-6}$ alkyl;

(iii) $R_4$ is H or $C_{1-4}$ alkyl;

(iv) $R_5$ is aryl optionally substituted with one or more groups independently selected from —C(=O)—$C_{1-6}$ alkyl and $C_{1-6}$-hydroxyalkyl;

(v) $R_6$ and $R_7$ are independently H or aryl optionally substituted with one or more groups independently selected from $C_{1-6}$ alkyl and halogen; and (vi) n is 1, 2, 3, or 4, in free or salt form;

E) a compound according to Formula IV':

Formula IV'

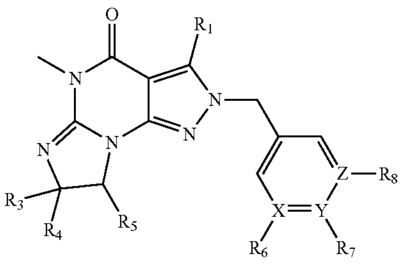

in free or salt form, wherein (i) $R_1$ is $C_{1-4}$alkyl, or —NH ($R_2$), wherein $R_2$ is phenyl optionally substituted with halo;

(ii) X, Y and Z are, independently, N or C;

(iii) $R_3$, $R_4$ and $R_5$ are independently H or $C_{1-4}$alkyl; or $R_3$ is H and $R_4$ and $R_5$ together form a tri-methylene bridge, (iv) $R_6$, $R_7$ and $R_8$ are independently:

H, $C_{1-4}$alkyl, pyrid-2-yl substituted with hydroxy, or

—$S(O)_2$—$NH_2$;

provided that when X, Y and/or Z are N, then $R_6$, $R_7$ and/or $R_8$, respectively, are not present; and when X, Y and Z are all C, then at least one of $R_6$, $R_7$ or $R_8$ is —$S(O)_2$—$NH_2$ or pyrid-2-yl substituted with hydroxy;

F) a compound according to Formula V:

Formula V

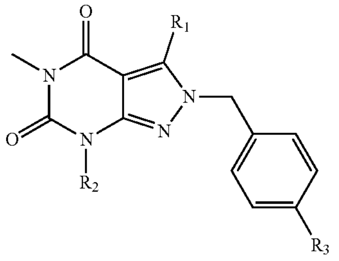

wherein (i) $R_1$ is —NH($R_4$), wherein $R_4$ is phenyl optionally substituted with halo;

(ii) $R_2$ is H or $C_{1-6}$alkyl;

(iii) $R_3$ is —$SO_2NH_2$ or —COOH;

in free or salt form; or

G) a compound according to Formula VI:

Formula VI

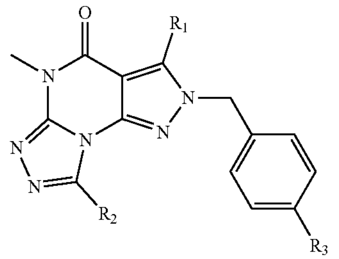

wherein (i) $R_1$ is —NH($R_4$), wherein $R_4$ is phenyl optionally substituted with halo;

(ii) $R_2$ is H or $C_{1-6}$alkyl;

(iii) $R_3$ is H, halogen, $C_{1-6}$alkyl, aryl optionally substituted with halogen, heteroaryl optionally substituted with halogen, or acyl, in free or salt form.

16. The method according to claim 1, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo [4,3-e]pyrimidin-4 (2H)-one monophosphate.

17. The method according to claim 15, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo [1,2-a]pyrazolo [4,3-e]pyrimidin-4 (2H)-one monophosphate.

18. The method according to claim 11, wherein the beta-adrenergic receptor antagonist is a beta-blocker; the antihyperlipoproteinemic is selected from the group consisting of an aryloxyalkanoic/fibric acid derivative, a resin/bile acid sequesterant, a HMG CoA reductase inhibitor, a nicotinic acid derivative, a thyroid hormone or thyroid hormone analog and combinations thereof; the antiarteriosclerotic is pyridinol carbamate; the antithrombotic and/or fibrinolytic agent is selected from the group consisting of anticoagulants, anticoagulant antagonists, antiplatelet agents, thrombolytic agents, thrombolytic agent antagonists, and combinations thereof; the blood coagulant is selected from the group consisting of thrombolytic agent antagonists, anticoagulant antagonists, and combinations thereof; the antiarrhythmic agent is selected from the group consisting of sodium channel blockers, repolarization prolonging drugs, calcium channel blockers, and combinations thereof; and the anti-hypertensive agent is selected from the group consisting of sympatholytic, alpha/beta blockers, alpha blockers, anti-angiotensin II agents, beta blockers, calcium channel blockers, vasodilators, and combinations thereof.

19. The method according to claim 1, wherein the PDE1 inhibitor is a compound according to Formula Ia:

Formula Ia

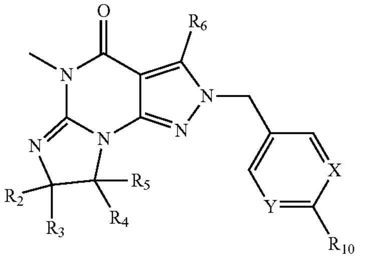

wherein (i) $R_2$ and $R_3$ are each methyl and $R_4$ and $R_5$ are each H;

(ii) $R_6$ is (optionally halo- or hydroxy-substituted) phenylamino;

(iii) $R_{10}$ is (optionally halo- or hydroxy-substituted) pyridyl; and

X and Y are independently C or N, in free or salt form.

20. The method of claim 19, wherein $R_6$ is halo-substituted phenylamino, $R_{10}$ is pyridyl, and X and Y are each C.

21. The method according to claim 15, wherein the PDE1 inhibitor is a compound according to Formula Ia:

Formula Ia

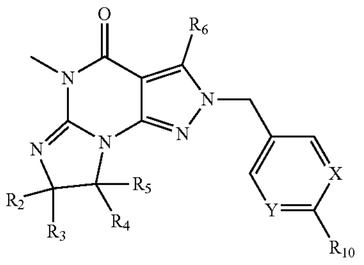

wherein (i) $R_2$ and $R_3$ are each methyl and $R_4$ and $R_5$ are each H;

(ii) $R_6$ is (optionally halo- or hydroxy-substituted) phenylamino;

(iii) $R_{10}$ is (optionally halo- or hydroxy-substituted) pyridyl; and

X and Y are independently C or N, in free or salt form.

22. The method of claim 21, wherein $R_6$ is halo-substituted phenylamino, $R_{10}$ is pyridyl, and X and Y are each C.

* * * * *